(12) United States Patent
Peyman

(10) Patent No.: US 7,833,966 B2
(45) Date of Patent: Nov. 16, 2010

(54) ENHANCED OCULAR NEUROPROTECTION AND NEUROSTIMULATION

(76) Inventor: Gholam A. Peyman, 1801 N. Norton, Tucson, AZ (US) 85719

( * ) Notice: Subject to any disclaimer, the term of this patent is extended or adjusted under 35 U.S.C. 154(b) by 0 days.

(21) Appl. No.: 11/561,912

(22) Filed: Nov. 21, 2006

(65) Prior Publication Data

US 2007/0078077 A1   Apr. 5, 2007

Related U.S. Application Data

(63) Continuation-in-part of application No. 11/263,737, filed on Nov. 1, 2005, and a continuation-in-part of application No. 11/183,355, filed on Jul. 18, 2005.

(51) Int. Cl.
*A61K 38/00* (2006.01)
(52) U.S. Cl. ........................................................ 514/2
(58) Field of Classification Search ...................... None
See application file for complete search history.

(56) References Cited

U.S. PATENT DOCUMENTS

| | | | |
|---|---|---|---|
| 4,079,038 A | 3/1978 | Choi et al. | 260/47 |
| 4,093,709 A | 6/1978 | Choi et al. | 424/19 |
| 4,131,648 A | 12/1978 | Choi et al. | 424/22 |
| 4,138,344 A | 2/1979 | Choi et al. | 252/1 |
| 4,180,646 A | 12/1979 | Choi et al. | 528/153 |
| 4,304,767 A | 12/1981 | Heller et al. | 424/78 |
| 4,946,931 A | 8/1990 | Heller et al. | 528/320 |
| 5,294,604 A | 3/1994 | Nussenblatt et al. | 514/11 |
| 5,387,589 A | 2/1995 | Kulkarni | 514/291 |
| 5,411,952 A | 5/1995 | Kaswan | |
| 5,457,182 A | 10/1995 | Widerrecht et al. | 530/402 |
| 5,770,607 A | 6/1998 | Honbo et al. | 514/302 |
| 5,773,019 A | 6/1998 | Ashton et al. | 424/423 |
| 5,952,371 A | 9/1999 | Baker et al. | 514/443 |
| 5,968,543 A | 10/1999 | Heller et al. | 424/425 |
| 6,004,565 A | 12/1999 | Chiba | 424/278.1 |
| 6,015,815 A | 1/2000 | Mollison | |
| 6,179,817 B1 | 1/2001 | Zhong | 604/265 |
| 6,218,423 B1 | 4/2001 | Ross et al. | |
| 6,238,799 B1 | 5/2001 | Opolski | 428/423 |
| 6,239,113 B1 | 5/2001 | Dawson et al. | 514/29 |
| 6,258,856 B1 | 7/2001 | Chamberlain et al. | 514/912 |
| 6,306,422 B1 | 10/2001 | Batich et al. | 424/423 |
| 6,331,313 B1 | 12/2001 | Wong et al. | |
| 6,413,536 B1 | 7/2002 | Gibson et al. | 424/423 |
| 6,436,906 B1 | 8/2002 | Or et al. | 514/29 |
| 6,440,942 B1 | 8/2002 | Or et al. | 514/29 |
| 6,462,026 B1 | 10/2002 | Or et al. | 514/30 |
| 6,462,071 B1 | 10/2002 | Castillejos | |
| 6,482,799 B1 | 11/2002 | Tuse et al. | |
| 6,489,335 B2 | 12/2002 | Peyman | 514/291 |
| 6,534,693 B2 | 3/2003 | Fischell et al. | |
| 6,596,296 B1 | 7/2003 | Nelson et al. | 424/426 |
| 6,613,355 B2 | 9/2003 | Ng et al. | 424/462 |
| 6,617,345 B1 | 9/2003 | Gregory et al. | 514/395 |
| 6,667,371 B2 | 12/2003 | Ng et al. | 525/462 |
| 6,670,398 B2 | 12/2003 | Edwards et al. | |
| 6,673,807 B1 | 1/2004 | Sakai et al. | |
| 6,713,081 B2 | 3/2004 | Robinson et al. | |
| 6,864,232 B1 | 3/2005 | Ueno | 514/9 |
| 6,872,383 B2 | 3/2005 | Ueno | 424/78.04 |
| 2001/0023245 A1 | 9/2001 | Okamoto | |
| 2003/0181692 A1 | 9/2003 | Ni et al. | |
| 2004/0106546 A1* | 6/2004 | Napoli | 514/11 |
| 2004/0162315 A1 | 8/2004 | Hellberg et al. | |
| 2005/0063996 A1 | 3/2005 | Peyman | |
| 2005/0063997 A1 | 3/2005 | Peyman | |
| 2005/0256065 A1* | 11/2005 | Harris et al. | 514/37 |

FOREIGN PATENT DOCUMENTS

| | | |
|---|---|---|
| AU | 17386/88 | 6/1988 |
| AU | 20350/92 | 7/1992 |
| CN | 1333018 | 1/2002 |
| CN | 1340358 | 3/2002 |
| CN | 1456350 | 11/2003 |
| DE | 19810655 | 9/1999 |
| EP | 1074255 | 2/2001 |
| EP | 1142566 | 10/2001 |
| EP | 0 532 862 | 3/2003 |
| JP | 07010752 | 1/1995 |
| JP | 1997030966 A | 2/1997 |
| JP | 09315954 | 12/1997 |
| JP | 10-218787 | 8/1998 |
| JP | 2001-064198 | 3/2001 |

(Continued)

OTHER PUBLICATIONS

Ang et al. Dry eye after refractive surgery. Curr Opin Ophthalmol. Aug. 2001;12(4):318-22.*

(Continued)

*Primary Examiner*—Elizabeth C. Kemmerer
*Assistant Examiner*—Gregory S Emch
(74) *Attorney, Agent, or Firm*—Joel B. German; Debra D. Condino; Allergan, Inc.

(57) ABSTRACT

Use of topically applied cyclosporine to enhance corneal sensitivity restoration rate in an eye of an individual after ocular surgery such as laser-assisted in situ keratomileusis (LASIK) in which nerves are severed.

19 Claims, 10 Drawing Sheets

FOREIGN PATENT DOCUMENTS

| WO | WO 89/01772 | 3/1989 |
|---|---|---|
| WO | WO 99/22722 | 5/1999 |
| WO | WO 99/34830 | 7/1999 |
| WO | WO 99/42104 | 8/1999 |
| WO | WO 00/66122 | 11/2000 |
| WO | WO 02/24234 | 3/2002 |
| WO | WO 02085928 | 10/2002 |
| WO | WO 03/017990 | 3/2003 |
| WO | 2003047525 A2 | 6/2003 |
| WO | WO 03/051385 | 6/2003 |
| WO | WO 2004/014373 | 2/2004 |
| WO | WO2004/027027 | 4/2004 |
| WO | WO 2004/043480 | 5/2004 |
| WO | WO 2004/096261 | 11/2004 |
| WO | 2005011813 A2 | 2/2005 |
| WO | WO 2005/011813 | 2/2005 |
| WO | WO2005/027906 | 3/2005 |
| WO | 2005030205 A1 | 4/2005 |
| WO | WO 2005/030205 | 4/2005 |

OTHER PUBLICATIONS

Kaminska et al. Molecular mechanisms of neuroprotective action of immunosuppressants—facts and hypotheses. J Cell Mol Med. Jan.-Mar. 2004;8(1):45-58.*

Tonra. Classical and novel directions in neurotrophin transport and research: anterograde transport of brain-derived neurotrophic factor by sensory neurons. Microsc Res Tech. May 15-Jun. 1, 1999, 45(4-5): 225-32.* http://www.accessdata.fda.gov/scripts/cder/drugsatfda/index.cfm?fuseaction=Search.Overview&DrugName=RESTASIS.*

LASIK Eye Surgery: What are the risks and how can I find the right doctor for me? Retrieved May 5, 2008 from US Food and Drug Administration web site at http://www.fda.gov/cdrh/lasik/risks.htm.*

Dua HS, Azuara-Blanco A. Corneal allograft rejection: Risk factors, diagnosis, prevention, and treatment. Indian J Ophthalmol 1999;47:3-9.*

Raivich et al. The making of successful axonal regeneration: Genes, molecules and signal transduction pathways. Brain Res Rev. Feb. 2007;53(2):287-311. Epub Oct. 31, 2006.*

Algvere PV, et al, *Long-term outcome of RPE allografts in non-immunosuppressed patients with AMD*, European J of Ophthalmology (1999), 9(3):217-320.

Anderson, DH, et al., *A role for Local Inflammation in the Formation of Drusen in the Aging Eye*, American Journal of Ophthalmology, vol. 134, No. 3, Sep. 2002, pp. 411-431.

Apel, a et al., *A subconjunctival degradable implant for cyclosporine delivery in corneal transplant therapy*, Current Eye Research, vol. 14, No. 8, Aug. 1995, pp. 659-667.

Aramant et al., *Retinal transplantation*, Science & Medicines (2000), 7:20-29.

D. Aron-Rosa, *Pulsed Nd:YAG lasers in ophthalmology*, Nd:YAG Laser Applications, pp. 34-48.

Bakalash, *Antigenic Specificity of Immunoprotective Therapeutic Vaccination for Glaucoma*, Invest Ophthalmol Vis Sci 2003; 44:3374-3381.

Carmo, et al., *Effect of Cyclosporin A on the blood-retinal barrier permeability in streptotocin-induced diabetes*, Mediators of Inflammation (2000), 9(5):243-248.

Chiou, *Topical Treatment of Ocular Hypertension, Glaucoma, Ischemic Retinopathy and Age-Related Macular Degeneration with Ophthalmic Formulation of Dopamine Antagonists*, U.S. Patent Publication No. US 2003/0069232, published Apr. 10, 2003.

Cicciarell et al, *Pharmacokinetics of subconjunctivally administered cyclosporine A. Local delivery prior to chemotherapy for retinoblastoma*, IOVS (Mar. 15, 2001), 42(4):S332.

Cooper et al., *Transscleral Delivery*, U.S. Patent Application Publication No. US2005/0064010, Published on Mar. 24, 2005, U.S. Appl. No. 10/945,682, filed Sep. 20, 2004.

Das et al., *The transplantation of human fetal neuroretinal cells in advanced retinitis pigmentosa patients: Results of a long-term safety study*, Experimental Neurology (1999), 157:58-68.

Del Cerro M et al, *Histologic correlation of human neural retinal transplantation*, Ophthalmology & Visual Science (2000), 41(10):3142-3148.

Steven H. Dewey, MD, *2003 PCO Update: Part 1—How the square-edged IOL prevenst posterior capsular opacification*, Cataract & Refractive Surgery Today, Sep. 2003, pp. 20-22.

Donnenfeld, ED, et al., *Cyclosporine provides effective treatment for dry eye*, Therapeutic Updates in Ophthalmology, Special Issue, Jul. 1999, pp. 1-3.

Enyedi LB, et al., *Pharmacokinetics and toxicity of an intravitreal device providing sustained release of cyclosporine (CsA) and dexamethasone (DEX)*, Investigative Ophthalmology and Visual Science, vol. 35, No. 4, 1994, p. 1906, and Annual Meeting of the Association for Research in Vision and Ophthalmology, Sarasota, FL, USA, May 1-6, 1994, abstract.

Enyedi, LB et al., *An intravitreal device providing sustained release of cyclosporine and dexamethasone*, Current Eye Research, May 1996, vol. 15, No. 5, pp. 549-557.

Freeman et al., *The Effects of FK506 on Retinal Ganglion Cells after Optic Nerve Crush*, Invest Opthalmol Vis Sci, 2000; 41:1111-1115.

Garweg, J et al., *Therapy of Goldmann-Favre's Vitreo-Retinal Degeneration with Cyclosporin A and Bromocriptine*, Klinische Monatsblatter for Augenheiljunde, vol. 199, No. 3, Sep. 1991, pp, 199-205.

Gilbard, JP, *EW Interview: Electrolyte balance is key to dry-eye product's success*, EyeWorld, Feb. 1999, pp. 20ff.

Goodman & Gilman, *The Pharmacological Basis of Therapeutics, 8th Ed.*, Pergamon Press, New York, 1990, pp. 1024-1033.

Grisolano et al., *Retinal Toxicity Study of Intravitreal Cyclosporin*, Opthalmic Surgery, Mar. 1986, 17:155-156.

Hageman et al., *Diagnostics and Therapeutics for Macular Degeneration-Related Disorders*, U.S. Patent Application Publication No. US 2002/0015957, published Feb. 7, 2002.

Jiang et al, *Corneal electroretinographic function rescued by normal retinal pigment epithelial grafts in retinal degenerative Royal College of Surgeons rats*, Investigative Ophthalmology & Visual Science (1994), 35(13):4300-4308.

Karacorlu et al., *Lack of toxicity of intravitreally administered interferon Alpha-2a*, Ophthalmic Surgery (1999), 23:833-835.

Kiryu et al. *In Vivo Evaluation of the Inhibitory Effects of Tacrolimus (FK506) on Leukocyte Accumulation During Retinal Ischemia Reperfusion Injury*, Poster Presentation—1247-B128.

Lai et al., *Local immunosuppression prolongs survival of RPE xenografts labeled by retroviral gene transfer*, IOVS (Sep. 2000), 41(10):3134-3141.

Lallemande, F, et al., *Cyclosporine A delivery to the eye: A pharmaceutical challenge*, European Jouranl of Pharmaceutics and Biopharmaceutics, 56 (2003), pp. 307-318.

Lipner, M, *Dry Eye 101: Developing etiologies and treatments for this widespread syndrome*, EyeWorld, Feb. 1999, pp. 19ff.

Lipper GM, et al, *Recent therapeutic advances in dermatology*, JAMA, vol. 283, No. 2, Jan. 12, 2000. pp. 175-177.

Lopez R et al., *Transplanted retinal pigment epithelium modifies the retinal degeneration in the RCS*, Ophthalmology & Visual Science (1989), 30:586-588.

Lund et al., *Subretinal transplantation of genetically modified cell lines attenuates loss of visual function in dystrophic rats*, PNAS (2001), 98(17):9942-9947.

Martin DF et al., *Synergistic Effect of Rapamycin and Cyclosporin A in the Treatment of Experimental Autoimmune Uveoretinitis*, The Journal of Immunology, 1995, 154:922-927.

Nicoletti et al., *The effects of deoxyspergualin on the development of diabetes in diabetes-prone BB rats*, Scandinavian Journal of Immunology (1992), 36(3):415-420.

Passos, E, et al., *Ocular Toxicity of Intravitreal Tacrolimus*, Ophthalmic Surgery and Lasers, Mar./Apr. 2002, vol. 33, No. 2, pp. 140-144.

PCT, *International Search Report*, PCT/US03/28315, mailed Jun. 15, 2004, 6 pages.

PCT, *International Search Report*, PCT/US2004/030186, mailed Feb. 8, 2005, received Feb. 14, 2005, 7 pg.
PCT, *International Search Report*, for PCT/2004/024054, filed Jul. 27, 2004, 7 pg.
Peyman, et al., *Intravitreal drug therapy*, Japanese Journal of Ophthalmology (1989), 33(4):392-404.
Peyman, GA, et al., *Implantation of a sustained-release ganciclovir implant*, Vitreoretinal Surgical Techniques, Martin Dunitz, Ltd., 2001, Chapter 45, pp. 521-531.
Peyman et al., *Intravitreal Surgery: Principles and Practice*, 2nd Edition, 1994, Appleton & Lange, Connecticut, pp. 443-452.
Gholam Peyman, MD, *Pupillary Membranes: Nd:YAG Capsulotomy*, Intravitreal Surgery, Norwalk CT, Appleton & Lange, 1994, pp. 253-257.
Peyman, *Treatment of Ocular Disease*, U.S. Patent Application Publication No. 2003,0018044, published Jan. 23, 2003, U.S. Appl. No. 10/247,220, filed Sep. 19, 2002.
Peyman, GA, et al., *Keratitis (Noninfectious)*, Principles and Practice of Ophthalmology, W.B. Saunders Company, 1980, pp. 446-449.
Revill et a., *Genetically Engineered Analogs of Ascomycin for Nerve Regeneration*, Journal of Pharmacology and Experimental Therapeutics, 2002; 302;1278-1385.
Schwartz et al., *Neuroprotection: a new treatment modality for glaucoma?*, Current Opinion in Ophthalmology, 2000; 11(2):107-111.
Schwartz et al., *Self-desctuctive and Self-protective Processes in the Damaged Optic Nerve: Implications for Glaucoma*, Invest. Ophthalnol Vis Sci, 2000: 41:349-351.
Schonfield and Kirst, *Macrolide Antibiotics*, Birkhausen, Basil, Switzerland, 2002, pp. 1-36.
Shen et al, *Combined effect of cyclosporine and sirolimus on improving the longevity of recombinant adenovirus-mediated transgene expression in the retina*, Archives of Ophthalmology (Jul. 2001), 119(7):1033-1043.
Stosic-Grujicic et al., *Leflunomide protects mice from multiple low dose streptozotocin (MLD-SA)-induced insulitis and diabetes*, Clinical & Experimental Immunology (1999), 117(1):44-50.
Ueno, *Use Of FK506 And Analogues For Treating Allergic Diseases*, U.S. Patent Application Publication No. US2005/0070468, Published on Mar. 31, 2005, U.S. Appl. No. 10/495,425, filed Nov. 20, 2002.
Ueno, *Method Of Treating Dry Eye With A Macrolide Compound*, U.S. Patent Application Publication No. US2004/0198763, Published on Oct. 7, 2004, U.S. Appl. No. 10/758,260, filed Jan. 16, 2004.
Ueno, *Local Ophthalmic Agent For Treatment Of Ocular Inflammation*, U.S. Patent Application Publication No. US2002/0187998, Published on Dec. 12, 2002, U.S. Appl. No. 10/120,515, filed Apr. 12, 2002.
Ueno, *Use of Macrolide Compounds for the Treatment of Dry Eye*, U.S. Patent Application Publication, published Jul. 10, 2003, U.S. Appl. No. 10/354,083, filed Jan. 30, 2003.
Ueno, *Composition For Topical Administration*, U.S. Patent Application Publication No. US2003/0044452, Published on Mar. 6, 2003, U.S. Appl. No. 10/187,013, filed Jul. 2, 2002.
Wakelee-Lynch, *Interferon may offer first drug therapy for diabetic retinopathy*, Diabetes Care (1992), 15(2):300-301.
Wax, *Is there a role for the Immune system in glaucomatous optic neuropathy?*, Current Opinion in Ophthalmology, 2000;11(2):145-150.
Wise, *Handbook of Pharmaceutical Controlled Release Technology*, Marcel Dekker, New York, 2000.
International Search Report and Written Opinion of the International Searching Authority. PCT/US2006/027713, mailed May 9, 2007.
Pepose, et a., Is There a Role for Neurotrophin Treatment of the Ocular Surface Following Laser in Situ Keratomilesusis (LASIK)?, Amer. Journal of Ophthalmology, Editorials, Jun. 2005, vol. 139, No. 6, pp. 1090-1094.
Kuehne, et al., Corneal Pharmacokinetics of Topically Applied Azithromycin and Clarithromycin, Oct. 2004, vol. 138, No. 4, pp. 547-553.
Reis, et al., Synergism of RAD and Cyclosporin A in Prevention of Acute Rate Comeal Allograft Rejection, Cornea, 2002, vol. 21, No. 1, pp. 81-84.
Mills, et. al. Topical FK-506 Prevents Experimental Corneal Allograft Rejection, Cornea, 1995, vol. 14, No. 2, pp. 157-160.
Wei, et al., Synthesis and neurotrophic activity of nonimmunosuppressant cyclosporin A derivatives, Bioorganic & Medicinal Chemistry Letters, 2004, Letter 14, pp. 4549-4551.
Heiligenhaus, et al., Treatment of HSV-1 stromal keratitis with topical cyclosporin A: a pilot study, Graefe's Arch Clin Exp Ophthalmol, 1999, vol. 237, pp. 435-438.
Hoffman, et al., Lokale Benhandlung Des Homhauttransplantates beim Menschen mit Cyclosporin A, Klin. Mbl. Augenheilk, 1985, vol. 187, No. 2, pp. 92-96.
Lee, et al., Nerve Growth Factor Concentration and Implications in Photorefractive Keratectomy vs Laser in situ Keratomileusis, Am J Ophthalmol, 2005; 139: pp. 965-971.
Perez-Santonja, et al., Corneal Sensitivity after photorefractive kertectomy and laser in situ keratomileusis for low myophia, Am J Ophthalmol, 1999; 127: pp. 497-504.
Erie, et al., Recovery of corneal subbasal nerve density after PRK and LASIK, Am J Ophthalmol, 2005; 140(6): pp. 1059-1064.
Calvillo, et al., Corneal reinnervation after LASIK: prospective 3-year longitudinal study, Invest Ophthalmol Vis. Sci., 2004; 45(11): pp. 3991-3996.
Nassaralla, et al., Effect of myopic LASIK on human corneal sensitivity, Ophthalmol, 2003; 110: pp. 497-502.
Martin, et al., Corneal hypoesthesia, Surv Ophthamol., 1998; 33: pp. 28-40.
Beuerman, et al., Sensory denervation of the rabbit cornea affects epithelial properties, Exp. Neurol, 1980; 69: pp. 196-201.
Lambiase, et al., Topical treatment with nerve growth factor for corneal neurotrophic ulcers, New England J. Medicine, 1998; 338: pp. 1174-1180.
Nagano, et al., Effects of Substance P and IGF-1 in Corneal Epithelial Barrier Function and Wound healing in a Rat Model of Neurotrophic Keratopathy, Invest Ophthalmol Vis Sci., 2003; 44: pp. 3810-3815.
Brown, et al., Neurotrophic and Anhidrotic Keratophathy Treated with substance P and Insulin-like Growth Factor 1, Arch Ophthalmol, 1997; 115: pp. 926-927.
Chikama, et al., Treatment of neurotrophic keratopathy with substance-P-derived peptide (FGLM) and insulin-like growth factor, Lancet, 1998; 351: pp. 1783-1784.
Fansa, et al., Stimulation of Schwann cell growth and axon regeneration of peripheral nerves by the immunosuppressive drug FK 506, Handchir Mikrochir Plast Chir., 1999; 31(5): pp. 323-329.
Carreau, et al., Comparative effects of FK-506, rapamycin and cyclosporin A, on the in vitro differentiation of dorsal root ganglia expants and septal cholinergic neurons, Neuropharmacology, 1997; 36(11-12): pp. 1755-1762.
Steiner, et al., Neurotrophic actions of nonimmunosuppressive analogues of immunosuppressive drugs FK506, rapamycin and cyclosporin A, Nature Medicine, 1997; 3(4): pp. 421-428.
Katsube, et al., Successful nerve regeneration and persistence of donor cells after a limited course of immunosuppression in rat peripheral nerve allografts, Transplantation, 1998; 66(6): pp. 772-777.
Revill, et al., Genetically engineered analogs of ascomycin for nerve regeneration, Journal of Pharmacology and Experimental Therapeutics, 2002; 302(3): pp. 1278-1285.
Salib, et al., Safety and efficacy of cyclosporine 0.05% drops versus unpreserved artificial tears in dry-eye patients having laser in situ keratomileusis, J Cataract Refract Surg, 2006; 32: pp. 772-778.
Kim, et al., Change in corneal sensitivity following laser in situ keratomileusis, J Cataract Refract Surg, 1999; 25: pp. 368-373.
Ishikawa, et al., Corneal sensation following excimer laser photorefractive keratectomy in humans, J Refract Corneal Surg, 1994; 10: pp. 417-422.
Freeman, et al., The Effects of FK506 on Retinal Ganglion Cells after optic nerve Crush, 2000; 41(5): pp. 1111-1115.
Schori, et al., Vaccination for Protection of Retinal Ganglion Cells against Death from Glutamate Cytotoxicity and Ocular Hypertension: Implications for Glaucoma, PNAS, 2001; 98(6): pp. 3398-3403.
Bakalash, et al., Antigenic Specificity of Immunoprotective Therapeutic Vaccination for Glaucoma, Investigative Ophthalmology Vis. Science, 2003; 44(8): pp. 3374-3381.

Linna, et al., Recovery of Corneal Nerve Morphology Following Laser in situ Keratomilesusis, Experiemental Eye Research, 1998; 66: pp. 755-763.

Kohlhaas, Corneal sensation after cataract and refractive surgery, J Cararact Refract Surg., 1998; 24: pp. 1399-1409.

Chung, et al., J Cataract Refract Surg, Confocal microscopic findings in a case of delayed-onset bilateral diffuse lamellar keratitiis after laser in situ keratomileusis, vol. 28, (2002), pp. 1467-1470.

Benitez-del-Castillo, et al., Decrease in Tear Secretion and Corneal Sensitivity After Laser In Situ Keratomileusis, Corneal, vol. 20, (2001), pp. 30-32.

Holly, The Iatrogenic Dry Eye and Its Management, CLES Meeting Jan. 23, 2003, revised Mar. 31, 2003, (See Slide 24 and the accompanying text).

Toda, et al., Dry Eye after Laser In Situ Keratomileusis, Am J. Ophthalmology, vol. 132, (2001) pp. 1-7.

International Preliminary Report on Patentability issued regarding International Application No. PCT/US2006/027713 (Nov. 2, 2007).

Hoffmann, F. et al., "Local Treatment of Corneal Transplant in Humans with Cyclosporin A," Klin. Mbl. 187, pp. 92-96 (1985) (in English language—see German reference "Lokale Behandlung des Hornhauttransplantates beim Menschen mit Cyclosporin A" previously disclosed).

Costantini et al., *Immunophilin Ligands and GDNF Enhance Neurite Branching or elongation from Developing Dopamine Neurons in Culture*, Experimental Neurology, 164:60-70 (2000).

Keep et al., *Introduction: Immunosuppressants as Neuroprotective Agents*, Immunosuppressant Analogs in Neuroprotection, Chapter I-Immunosuppressants, Neurologic Disorders, and Neuroprotection, Eds. Borlongan et al., Humana Press Inc., Totowa NJ, pp. 3-32 (2002).

Peyman, *Ocular Solutions*, U.S. Application Publication No. 2005/0063997, published Mar. 24, 2005, U.S. Appl. No. 10/752,124, filed Jan. 6, 2004.

Peyman, *Treatment of Ocular Disease*, U.S. Application Publication No. 2005/0025810, published Feb. 3, 2005, U.S. Appl. No. 10/631,143, filed Jul. 31, 2003.

Peyman, *Treatment of Ocular Disease*, U.S. Application Publication No. 2004/0092435, published May 13, 2004, U.S. Appl. No. 10/289,772, filed Nov. 7, 2002.

Peyman *Ocular Solutions*, U.S. Application Publication No. 2005/0063996, published Mar. 24, 2005, U.S. Appl. No, 10/667,161, filed Sep. 19, 2003.

Battat et al., Effects of laser in situ keratomileusis on tear production, clearance, and the ocular surface. Ophthalmology, 108:1230-1235 (2001).

Erie et al., Corneal wound healing after photorefractive keratectomy: A 3-year confocal microscopy study. Trans AM Ophthalmol Soc, 101:294-333 (2003).

Moilanen et al., Long-term corneal morphology after PRK by in vivo confocal microscopy. Invest Ophthalmol Vis Sci, 44:1064-1069 (2003).

Calvillo et al., Corneal reinnervation after LASIK: Prospective 3-year longitudinal study. Invest Ophthalmol Vis Scie, 45:3991-3996 (2004).

Lee et al., Reinnervation in the cornea after LASIK. Invest Ophthalmol Vis Sci, 43:3660-3664 (2002).

Lee et al., Comparison of corneal nerve regeneration and sensitivity between LASIK and laser epithelial keratomileusis (LASEK). Am J Ophthalmol, 141:1009-1015 (2006).

Anderson et al., Histologic and ultrastructural findings in human corneas after successful laser in situ keratomileusis. Arch Ophthalmol, 120:288-293 (2002).

Latvaia et al., Corneal wound healing and nerve morphology after excimer laser in situ keratomileusis in human eyes. J Refract Surg, 12:677-683 (1996).

Peyman et al, "Cyclosporine0.05% Ophthalmic Preparation to Aid Recovery From Loss of Corneal Sensitivity After LASIK", J. Refract. Sur., 24: 337-343 (2008).

C. de Paiva and S. Pflugfelder, "Corneal Epitheliopathy of Dry Eye Induces Hyperesthesia to Mechanical Air Jet Stimulation", Am.J. Ophthal., 137:109-115 (2004).

Merck Manual of Diagnosis and Therapy, "Refractive Error" (2007), accessed online at http://www.merck.com/mmpe/sec09/ch099/ch099a.html.

Merck Manual of Diagnosis and Therapy, "Refractive Surgery" (2007), accessed online at http://www.merck.com/mmpe/sec09/ch099/ch099a.html.

Refractive Surgery and Corneal Modification Definitions ("AOA Definitions") available online at http://www.aoa.org/ x4749.xml, Retrieved Aug. 2, 2010.

American Academy of Ophthalmology, "Vision Correction" (2009), available online at http://www.geteyesmart.org/eyesmart/correction/index.cfm.

Eye Bank Association of America, "2005 Eye Banking Statistical Report," p. 1-21.

American Academy of Ophthalmology, "Answer Archive," accessed online at http://www.geteyesmart.org/eyesmart/ask/questions/090731d.cfm, Retr. Aug. 2, 2010.

Stevenson et al, "Efficacy and Safety of Cyclosporin A Ophthalmic Emulsion in the Treatment of Moderate-to-sever Dry Eye Disease", Ophthalmology, 107:5, 967-974 (2000).

Wilson, "Laser In Situ Keratomileusis-induced (Presumed) Neurotrophic epitheliopathy", Ophthalmology, 108:6, 1082-1087 (2001).

Savini et al, "Ocular Surface Changes in Laser in situ Keratomileusis-induced Neurotrophic Epitheliopathy", J. Refract. Sur., 20:6 803-809 (2004).

Wilson et al, "Laser In Situ Keratomileusis-Induced Neurotrophic Epitheliopathy", Am. J. Ophthalmol., 132:405-406 (2001).

Restasis® Orange Book Listing, U.S. Food and Drug Administration, Retr. Aug. 2, 2010.

Restasis® Prescription Information Sheet, Allergan, Inc.,Feb. 2010.

Belmonte, Eye Dryness Sensations After Refractive Surgery: Impaired Tear Secretion or "Phantom" Cornea?, J. Refract. Surg., 23:598-602 (2007).

Belmonte, "Neural basis of sensation in intact and injured corneas", Experimental Eye Research 78, 513-525-2004.

Tuisku et al., " Dry Eye and Corneal Sensitivy After High Myopic LASIK ?" J. Refract. Surg., 23:338-342 (2007).

P. Rosenthal et al., "Corneal Pain without Stain: Is it Real?", Ocular Surface, 7(1):28-40 (2009).

Ambrósio et al., "LASIK-associated Dry Eye and Neurotrophic Epitheliopathy: Pathophysiology and Strategies for Prevention and Treatment", J. Refract. Surg., 24:396-407 (2008).

Steiner et al, Neurotrophic actions of nonimmunosuppresive analogues of immunosuppressive drugs FK506, rapamycin and cyclosporine A, Nature Medicine, 3-4-421-428, 1997.

Carreau et al., Comparative Effects of FK-506, Rapamycin and Cycosporin A, on the in vitro Differentiation of Dorsal Root Ganglia Explants and Septal Cholinergic Neurons, Neuropharmacology, 36:1755-1762 (1998).

Lutsep et al, "Current Status of Neuroprotective Agents in the Treatment of Acute Ischemic Stroke", Curr. Neurol. and Neurosci. Reports, 1:13-18 (2001).

* cited by examiner

ENHANCED OCULAR NEUROPROTECTION AND NEUROSTIMULATION

This application is a Continuation-In-Part of U.S. patent application Ser. No. 11/263,737 filed Nov. 1, 2005, which is a Continuation-In-Part of U.S. patent application Ser. No. 11/183,355 filed Jul. 18, 2005, each of which is expressly incorporated by reference herein in its entirety.

FIELD OF THE INVENTION

Methods to enhance corneal sensation and/or reduce scarring after ocular surgery, and to enhance ocular neuroprotection and/or neurostimulation to reduce neurodegenerative changes that may be associated with glaucoma or other ocular diseases.

BACKGROUND

Methods and compositions that enhance a patient's condition prophylactically or therapeutically, or after ocular surgery are desirable.

SUMMARY OF THE INVENTION

One embodiment is a composition comprising at least one neuro-stimulatory factor in a pharmaceutically effective concentration and formulation for non-systemic localized ocular administration and effect. The composition contains macrolides or may further be modified to contain one or more macrolides if not already present. It may be formulated with excipients for topical ocular administration, administration in an ocular device or delayed release matrix, administration by subconjunctival or intraocular injection, etc. It may be contained in an intraocular implant, an intraocular lens, or a contact lens. The neuroprotective or neurostimulatory factor may be a macrolide, which may be cyclosporine, tacrolimus, sirolimus, everolimus, pimocrolous, or others; macrolide analog; neurotrophin; and/or a neuropoietic factor. In some embodiments, one or more other agents may also be included, for example, an antioxidant, steroid, non-steroidal anti-inflammatory drug, antibiotic, anti-proliferative agent, anti-cell migration agent, anti-prostaglandin, anti-angiogenic agent, vitamin, mineral, growth factor, or cytokine.

Another embodiment is an ocular method comprising administering to a patient after ocular surgery a composition comprising at least one neurostimulatory factor, which also encompasses a macrolide or macrolide analog with neurostimulatory activity, in a pharmaceutically effective concentration and formulation for non-systemic localized ocular administration. The composition may be ocularly administered topically, subconjunctivally, intraocularly, by implantation in a device or a lens, or from a contact lens. The composition may be administered to the patient after corneal surgeries or procedures such as laser-assisted in situ keratomileusis (LASIK), laser-assisted in situ epithelial keratomileusis (LASEK), photorefractive keratectomy (PRK), keratoplasty (total corneal transplant, partial corneal transplant), etc.

Another embodiment is an ocular method whereby a macrolide or macrolide analog is administered to a post-ocular surgery patient to reduce or minimize ocular scarring. The macrolide may be present as a component in a composition administered to provide a neuroprotective and/or neurostimulatory effect. Alternatively, the macrolide may be administered to reduce or minimize scarring following any type of ocular surgery, including but not limited to glaucoma surgery, retinal detachment repair surgery, and corneal surgery.

Another embodiment is a method for administering a macrolide, macrolide analog, neurotrophin, and/or neuropoietic agent prophylactically to patients having or at risk for developing an ocular neurologic or neurosensory disease, or therapeutically to patients with an ocular neurologic or neurosensory disease, either alone or in conjunction with other therapy. Glaucoma is a non-limiting example of an ocular disease with a neuroassociated component. Retinitis pigmentosa is a non-limiting example of an ocular disease with a neurosensory component.

Another embodiment discloses topical ocular cyclosporine to enhance recovery of corneal sensitivity in patients after corneal incisional or lamellar surgeries or procedures such as LASIK, LASEK, PRK, etc. Topical ocular cyclosporine applied post-LASIK surgery has reduced inflammatory processes and enhanced secretion of a tear film component, thereby reducing symptoms of dry eye; however, topical ocular cyclosporine efficacy in enhancement of post-LASIK corneal sensitivity recovery rate has not previously been demonstrated prior to the present invention. Topical ocular cyclosporine effect on enhancement in ocular nerve regeneration has not previously been suggested prior to the present invention.

These and other embodiments of the invention will be further appreciated in view of the following drawings, detailed description, and examples.

DETAILED DESCRIPTION

Figure 1:
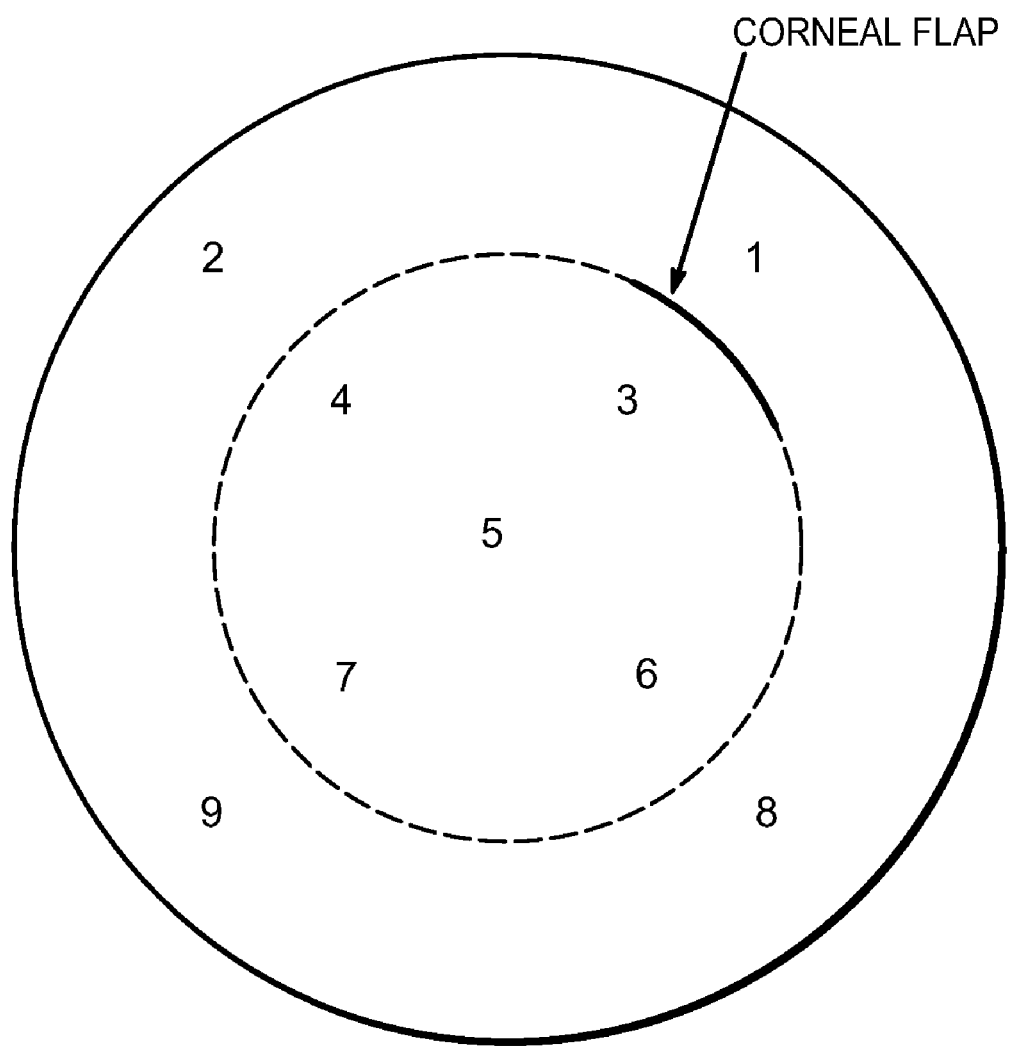
FIG. 1 diagrammatically shows nine areas of an eye where post-surgical corneal sensitivity measurements were assessed.

One embodiment is a method to enhance patient recovery after ocular surgery or other trauma by enhancing corneal sensation, ocular nerve regeneration, and/or re-enervation. The method enhances the restoration rate and restores at least partially the loss of corneal sensation that occurs following corneal procedures during which nerves are severed. The method also reduces or minimizes post-surgical scarring that could lead to corneal opacification, reduced vision, and/or other complications, by compositions with a macrolide or macrolide analog component. For example, it could be used to reduce or minimize scarring of the conjunctiva that occurs after glaucoma surgery, or scarring that may lead to proliferative vitreal retinopathy (PVR) after retinal detachment repair surgery, or scarring that occurs after corneal surgery. While not being bound by a specific theory, a method to reduce or minimize post ocular-surgery scarring may enhance ocular sensation, nerve regeneration, and/or re-enervation, possibly by minimizing scar tissue that may impair nerve growth, nerve cell connections, etc. The method thus leads to enhanced recovery following ocular surgery.

One embodiment is a method to enhance ocular neuroprotection and/or neurostimulation in or to an eye by locally administering to the eye, in a non-systemic manner, a composition of at least one neuroprotective or neurostimulatory factor. The neuroprotective or neurostimulatory factor may be administered either alone or in combination with other agents such as neurotrophins, neuropoietins, etc. The neurostimulatory and/or neuroprotective factor may be, but is not limited to, a macrolide, a macrolide analog, a neurotrophin, and/or a neuropoietic agent.

One embodiment provides localized ocular administration of macrolides and/or macrolide analogs, either alone or in combination with other neuro-stimulatory agents such as neurotrophins, neuropoietins, etc. The macrolides and/or macrolide analogs may or may not have neuro-stimulatory activity.

"Corneal anesthesia" is an unwanted consequence in some patients who have undergone an ocular surgical procedure. Such procedures include laser-assisted in situ keratomileusis (LASIK), laser-assisted in situ epithelial keratomileusis (LASEK), photorefractive keratectomy (PRK), and keratoplasty, i.e., corneal transplant (total or partial). In some of these types of procedures, the surgeon creates a micro-thin flap (shown in FIG. 1) in the cornea and stroma to access the cornea. For example, LASIK is a refractive procedure in which a laser is used to both create the flap and then to sculpt the underlying corneal tissue to form a more effective shape. LASIK involves mechanical section of the corneal nerve during creation of the flap to expose the stromal bed for laser abiation.

The stromal corneal flap may be created using a femtosecond computer-guided laser, or a hand-held microkeratome with an oscillating metal blade. The flap is then folded open to provide access to the cornea for the procedure, after which the flap is then closed by returning to its original position. It seals without stitches and heals shut. The flap promotes post-surgical healing, patient comfort, and improved vision. If the flap is not of the proper thickness (e.g., too thick, too thin, or irregular), the patient's healing and quality of vision may be compromised.

In creating the LASIK flap, the nerves that enervate the surface of the cornea are mechanically dissected. This results in corneal nerve destruction and, consequently, reduced corneal sensitivity within the LASIK flap area. One study reported that the number of sub-basal and stromal nerve fiber bundles in the corneal flap decreased 90% immediately following surgery. Although the sub-basal nerve fiber bundles gradually returned, their number remained less than half of the pre-surgical number. The loss of corneal sensation caused by a decrease in the number of enervating nerves, and/or their function, may last up to about six months after the original procedure. Diabetic patients are particularly prone to decreased corneal nerve function, yet are a group of patients in frequent need of corneal transplants.

After surgery corneal nerve fibers gradually re-innervate the cornea, and corneal sensation is slowly restored. Complete corneal recovery after LASIK is a very slow process, and compromised corneal sensitivity is a precarious situation. A low corneal sensitivity threshold is required for early detection of foreign bodies, injury, and/or pathological changes. The loss of normal corneal sensation can compromise the protective blink reflex, delay epithelial wound healing, decrease tear flow, and be associated with neurotrophic keratilis, sterile corneal melts, and/or infectious keratides. At least six months is necessary for full restoration of corneal sensitivity, even longer for patients with higher degrees of myopia. Complete nerve restoration (i.e., re-enervation) to pre-surgical density levels is not complete before five years post-LASIK.

In general, LASIK, LASEK, PRK, and other types of corneal incisional or lamellar surgeries or procedures are performed on an outpatient basis. Prior to surgery, a topical anesthesia is applied to the eye, and a speculum is placed to separate the eyelids.

LASEK is similar to LASIK but in LASEK a corneal epithelial flap is cut and ablation is performed on the surface, followed by repositioning of the epithelial flap.

In PRK, the surface corneal epithelia are removed. Laser ablation to reshape the corneal surface commences, with preprogrammed parameters based upon specific patient vision characteristics (e.g., myopia, hyperopia, astigmatism, etc.).

Laser thermal keratoplasty (LTK) uses a holmium-YAG laser energy to reshape the cornea. Laser energy is applied in a predetermined pattern to shrink collagen fibers and thus steepen the cornea. Ocular tissue is neither cut nor removed.

Conductive keratoplasty (CK) is a non-laser based ocular procedure. It does not involve cutting the cornea, and reshapes the cornea using low-level radiofrequency (RF) energy administered through a fine probe. Using the probe, RF energy is applied to specific sites in a pre-set marked circular pattern (e.g., using a dye) on the outer cornea to shrink or ablate small areas of corneal tissue. The circular shrinkage pattern creates a constrictive band, thus increasing the overall curvature of the cornea.

In keratoplasty or penetrating keratoplasty, the cornea is either partially or totally replaced with donor cadevar corneal tissue. The surgery is typically performed on an outpatient basis under local injectable anesthesia. Although there is some risk of rejection, the cornea is essentially avascular, which reduces such risk. Candidates for keratoplasty or penetrating keratoplasty include patient with keratoconus (inherited corneal thinning) with visual distortion, with Fuch's dystrophy (corneal clouding, either heriditary or acquired) with vision loss, and/or corneal scarring (e.g., due to injury). Full visual recovery takes up to a year post-surgery.

Corneal sensation is reduced in each of the described procedures; corneal sensation is reduced to a greater extent in procedures that involve cutting compared to procedures that do not involve cutting.

Upon completion of any of these procedure, the duration typically being less than one minute, medicaments, typically anti-inflammatory agents and/or antibiotics, are topically applied to the corneal surface. In procedures that involve cutting, a contact lens is then placed on the eye.

An example of a medication administration protocol used in the inventive method follows. At the completion of the LASIK procedure, one drop of cyclosporine (0.05% w/v) composition, such as a liquid solution or emulsion, was administered onto the corneal surface(s) of the eye(s). After at least ten minutes one drop of an anti-inflammatory agent (e.g., prednisolone) and one drop of an antibacterial agent (e.g., moxifloxacin) were administered to the eye. This administration protocol was followed hourly on the day of surgery while the patient was awake. An ocular lubricant was also administered to the corneal surface hourly after surgery and then as needed to alleviate dry eye sensation. Other suitable anti-inflammatories, antiirritants, antibiotics, and ocular lubricants may be used, as known to one skilled in the art.

On the day after surgery one drop of cyclosporin (0.05% w/v) composition was administered to the eye twice a day at intervals of about 12 hours. Then, for up to about six months or more depending upon the progress of recovery, a drop of the antiinflammatory/antiirritant and/or antibiotic was administered to the eye four times daily for one week and then twice a day for two days, and then once a day for two days. The medications were administered to the eye before a lens was placed in the eye. The eye lubricant was uses on an as needed basis. The protocol was varied according the progress of recovery, the sensitivity of the patient to the medications, and other factors as known to one skilled in the art.

One drop of drop of cyclosporine (0.05% w/v) composition (liquid solution or emulsion) has a volume of about 0.065 ml (65 μl), which would contain about 32.5 μg cyclosporine. Solutions of cyclosporine may have concentrations ranging from about 0.01% w/v to about 1.0% w/v cyclosporine, thus the amount of cyclosporine that can be administered in a drop of solution to enhance ocular neuroprotection ranges from about 6.5 μg to about 650 μg. In other embodiments the concentration of cyclosporine ranged from about 0.05% to about 0.5% and 0.05% to about 0.1%, resulting in amounts of cyclosporine administered from about 6.5 μg to about 325 μg and from about 6.5 μg to about 65 μg. One skilled in the art will know the amount of cyclosporine delivered will vary with the volume (size) of the drop of solution which is determined by physiochemical factors such as the number of components in solution or emulsion (i.e., excipients, surfactants, chelators, etc.), surface tension, aperture size of delivery apparatus, etc. Solutions of cyclosporine are commercially available (e.g., RESTASIS® (0.05% cyclosporine ophthalmic emulsion, Allergen).

Patients were typically evaluated at post-surgical intervals of one day, three days, one week, one month, two to three months, and four to six months. The bandage contact lens was typically removed on the second or third post-operative day when the epithelium had healed. Most patients required eye drops to control healing only during the first six to twelve weeks, but other patients, usually those with greater refractive error, required topically applied medicaments for up to six months or more following surgery.

After any of these corneal surgeries, patients may experience problems relating to the loss of ocular sensitivity or sensation. For example, decreased ocular nerve function makes the cornea prone to trauma, which in turn can lead to infection. It reduces the usual blink mechanism that is required to keep the corneal surface moist, leading to drying and sloughing of the corneal epithelium. This, in turn, causes cloudiness of the flap, prones the flap to infection by enteral pathogens because of loss of barrier, and reduces vision.

One embodiment of the invention is a method for ameliorating or restoring loss of corneal sensation, enhancing ocular nerve regeneration, and/or restoring nerve function (re-enervation) in the eye of a patient by providing locally to the eye a composition comprising at least one neuroprotective and/or neurostimulatory factor. Another embodiment is a method for prophylactically administering, to an eye of a patient at risk for an ocular neurologic and/or neurosensory pathology, a neuroprotective and/or neurostimulatory factor to ameliorate or restore loss of corneal sensation, enhance ocular nerve regeneration, and/or provide reeneravation.

One embodiment of the invention locally administers one or more agents that enhance corneal sensation, possibly by nerve regeneration and/or enervation. In one embodiment, one or a combination of macrolides, including macrolide analogues, is administered, the macrolide and/or analogue having neuro-stimulatory activity. In another embodiment, one or a combination of macrolides is administered with one or more agent(s) that enhance corneal nerve stimulation. Such neurostimulatory agents may increase nerve cell quantity, functional quality, or combinations of these. One skilled in the art will appreciate that enhancement refers to any qualitative and/or quantitative improvement in corneal sensation and/or ocular neurological function following surgery regardless of degree.

One embodiment of the invention is a composition containing a neurostimulatory or neuroprotective macrolide, macrolide analog, neurotrophin, and/or neuropoietic factor that may be administered prophylactically to patients having or at risk for developing glaucoma, retinitis pigmentosa, or other neurosensory or neurodegenerative disease, or may be administered to patients with glaucoma or retinitis pigmentosa, either alone or in conjunction with other therapy.

Glaucoma is a general term for several types of a painless ocular condition that, left untreated, can result in partial or complete vision loss. It is characterized by elevated intraocular pressure, considered by one skilled in the art as a pressure greater than about 21.5 mm Hg. The higher the intraocular pressure, the greater the likelihood of optic nerve damage and visual field loss. In glaucoma monitoring or therapy, the neurodegenerative component should be considered in addition to therapy for increased intraocular pressure, such as protection of retinal ganglion cells (RGC).

Known risk factors for glaucoma include age (elevated risk for individuals over age 60), race (elevated risk for African Americans over age 40), a family history of glaucoma, individuals with diabetes, severe nearsightedness, long-term corticosteroid use, previous eye injury, and/or increased intraocular pressure. One risk factor may suffice for prophylactic administration of a neuroprotective and/or neurostimulatory agent as described herein, and risk factors may alter over time, as known to one skilled in the art.

In monitoring, diagnosing, and/or treating patients with glaucoma, attainment of decreased intraocular pressure is a necessary but insufficient goal. This is because a component of glaucoma is neurologic damage to the optic nerve and ganglion cell death, so that its neurodegenerative aspects must be considered. Even patients with normal intraocular pressure may develop glaucoma-like changes. Further, retinal ganglion cells may be more sensitive to increased intraocular pressure, whereas other ocular cells may be better able to withstand increased intraocular pressure.

Retinitis pigmentosa is a general term that encompasses a disparate group of disorders of rods and cones. Because retinitis pigmentosa affects these retinal sensory structures, prophylactic or therapeutic administration of neuroprotective or neurostimulatory agents may reduce decreased visual field and other adverse effects.

In one embodiment, a patient is prophylactically or therapeutically administered a neurostimulatory and/or neuroprotective macrolide, macrolide analog, neurotrophin, and/or neuropoietic agent. The inventive method may prevent or delay an increase in intraocular pressure, may reduce associated nerve loss, may confer protection on retinal sensory cells, etc. Administration may be by any ocular route. One example is topical application, with the neurostimulatory and/or neuroprotective agent(s) administered in a formulation of eye drops, cream, ointment, gel, salve, etc. Another example is intraocular injection with the neurostimulatory and/or neuroprotective agent administered subconjunctivally, intravitreally, retrobulbarly, within the crystalline lens via piercing the lens capsule as described in co-pending U.S.

patent application Ser. No. 11/103,283 which is expressly incorporated by reference herein, etc. Another example provides the neurostimulatory and/or neuroprotective agent to the eye on or in a formulation such as a liposome, microsphere, microcapsule, biocompatible matrix, gel, polymer, nanoparticle, nanocapsule, etc. Another example provides the neurostimulatory and/or neuroprotective agent on or in a device such as a device for transscleral delivery as described in co-pending U.S. patent application Ser. No. 11/105,756, or another intraocular device using, for example, iontophoresis or another type of release mechanism (controlled or not controlled), as known by one skilled in the art. Another example provides the neurostimulatory and/or neuroprotective agent in conjunction with gene therapy, as known by one skilled in the art.

A topical formulation may be administered by any ophthalmogical vehicle, as know to one skilled in the art. Examples include, but are not limited to, eye droppers, satchels, applicators, etc. The amount and concentration of the formulation may depend upon the diluent, delivery system or device selected, clinical condition of the patient, side effects expected, stability of the compounds of the composition, presence and severity of other pathology, dosing frequency, active agent, etc.

For topical administration, examples of concentrations that may be used include but are not limited to, less than 1 μg/mL, 1 μg/mL to 5 μg/mL, 5 μg/mL to 10 μg/mL, 10 μg/mL to 50 μg/mL, 50 μg/mL to 100 μg/mL, 100 μg/mL to 0.5 mg/mL, 0.5 mg/mL to 2.5 mg/mL, 1 mg/mL to 5 mg/mL, 5 mg/mL to 10 mg/mL, 10 mg/mL to 15 mg/mL, 15 mg/mL to 30 mg/mL, and greater than 30 mg/mL. For topical administration, examples of dosing regimens that may be used include but are not limited to, hourly, half-daily, daily, weekly, biweekly, monthly, quarterly, three times a year, twice a year, yearly, every two years, every three years, etc. Intervals between doses may be regular or varied. As one example, doses may be administered hourly or daily pre- and post-surgery for one week, for several weeks, or for several months, then may be administered twice a year or once a year until the desired neurostimulation and/or neuroprotection is achieved. As another example, doses may be administered daily or weekly pre- and/or post-surgery for one week, for several weeks, for several months, or for several years until the desired neurostimulation and/or neuroprotection is achieved.

Ganglion cells in the retina (RGC) that have been damaged (e.g., by elevated intraocular pressure) undergo apoptosis, also referred to as programmed cell death. The macrolide tacrolimus, systemically administered, conferred neuroprotection on RGC by interfering with apoptotic mechanisms, as disclosed in Freeman and Grosskreutz Investigative Ophthalmology & Visual Science:41, 1111 (2000), which is expressly incorporated by reference herein in its entirety. As a result of programmed cell death, RGC release compounds whose presence and/or concentration may result in toxicity, remove desirable agents and/or alter cell signaling; these compounds include cytokines, the excitatory neurotransmitter glutamate, $Ca^{2+}$ binding proteins, FK 506 (tacrolimus) binding proteins, and others. Thus, ocular administration of a neurostimulatory and/or neuroprotective macrolide, macrolide analog, neurotrophin, and/or neuropoietic factor may reduce or inhibit subsequent effects of the released cytokines, glutamate, etc. that are part of the neurodegenerative processes associated with glaucoma and/or retinitis pigmentosa. For example, macrolides tacrolimus and cyclosporine are potent immunosuppressants that inhibit T-cell activation by interfering with signal transduction. In vitro, tacrolimus binds to and inhibits the activity of the immunophilin FK 506-binding protein (FKBP), an isomerase that functions in signal transduction and cell communication. Reducing apoptotic mechanisms would reduce such processes, and thus protect or delay neurosensory impairment or neurodegenerative damage.

Such administration of macrolides may be alone or may be in conjunction with other agents used to reduce intraocular pressure in patients with elevated intraocular pressure due to ocular hypertension or open-angle glaucoma. For example, administration may be included with a current drug regimen, or at different intervals than a current regimen, or for a set duration, etc; all these are examples of administration in conjunction with other agent. Examples of known drugs include, but are not limited to, Diamox® (acetazolamide (N-(5-sulfamoyl-1,3,4-thiadiazol-2-yl)acetamide), an inhibitor of carbonic anhydrase, Wyeth, Madison N.J.); Timoptic® (timolol maleate ophthalmic solution, Merck, Whitehouse Station N.J.), Xalatan® (latanaprost ophthalmic solution, Pfizer, Groton Conn.); Copaxone® (Teva Pharmaceuticals, Petah Tiqva, Israel); Memantine (Allergan, Irvine Calif.); Alphagan® P (brimonidine tartrate ophthalmic solution; Allergan); and others known to one skilled in the art. In this embodiment, the inventive method may use macrolides to potentiate the action of current treatments. For example, acetazolamide may assist in normal polarization of cell membranes, so the effect of local ocular treament with acetazolamide and a neuroprotective macrolide or agent, is reduced apoptic effects and normalized polarization of sensory retinal ganglion cells. The dual action may be additive or synergistic.

Macrolides encompassed by the invention are those known by one skilled in the art, as well as analogs and derivatives. These are disclosed in, for example, co-pending U.S. patent application Ser. Nos. 10/667,161 and 10/752,124. Macrolides and their analogues that may be administered include the following.

Cyclosporine (Cyclosporin A, topical formulation Arrestase®, Allergan Inc.) is a cyclic peptide produced by *Trichoderma polysporum*. It is available commercially, for example, from Sigma-Aldrich (St. Louis Mo.). It is an immunosuppressant and acts in a particular subset of T lymphocytes, the helper T cells. Cyclosporine exerts an immunosuppressant effect by inhibiting production of the cytokine interleukin 2. Each of cyclosporine and tacrolimus, another immunosuppressant, produces significant renal and hepatic toxicity when each is administered systemically; because of this toxicity, they are not administered together. The use of cyclosporine as a specific medicament for treatment of ocular disease with reduced toxicity is described in co-pending U.S. patent application Ser. No. 10/289,772. Cyclosporine is commercially available as a 0.05% emulsion for ophthalmic application under the trademark RESTASIS® (Allergan). Its indication is increased tear production in patients with ocular inflammation associated with keratoconjunctivitis sicca (chronic dry eye).

Tacrolimus (Prograf®, previously known as FK506), a macrolide immunosuppressant produced by *Streptomyces tsukubaensis*, is a tricyclo hydrophobic compound that is practically insoluble in water, but is freely soluble in ethanol and is very soluble in methanol and chloroform. It is available under prescription as either capsules for oral administration or as a sterile solution for intravenous administration. The solution contains the equivalent of 5 mg anhydrous tacrolimus in 1 ml polyoxyl 60 hydrogenated castor oil (HCO-60), 200 mg, and dehydrated alcohol (USP, 80.0% $^{v/v}$), and must be diluted with a solution of 0.9% NaCl or 5% dextrose before use.

Sirolimus, also known as rapamycin, RAPA, and Rapamune®, is a triene macrolide antibiotic derived from *Strepto-*

*myces hydroscopicus* and originally developed as an antifungal agent. Subsequently, it has shown anti-inflammatory, antitumor, and immunosuppressive properties. Pimecrolimus, also known as ascomycin, Immunomycin, and FR-900520, is an ethyl analog of tacrolimus and has strong immunosuppressant properties. It inhibits Th1 and Th2 cytokines, and preferentially inhibits activation of mast cells, and is used to treat contact dermatitis and other dermatological conditions. Sirolimus and pimecrolimus are commercially available, e.g., A.G. Scientific, Inc. (San Diego Calif.).

Regarding its immunosuppressive potential, sirolimus has some synergetic effect with cyclosporine. It has been reported that sirolimus has a different mode of action compared to cyclosporine and tacrolimus. All three agents are immunosuppressants which affect the action of immune cell modulators (cytokines), but do not affect the immune cells themselves. However, while all three agents affect immune cell modulators, they do so differently: cyclosporine and tacrolimus prevent synthesis of cytokine messengers, specifically interleukin-2, while sirolimus acts on cytokine that has already been synthesized, preventing it from reaching immune cells.

Sirolimus inhibits inflammation by acting on both T-lymphocytes and dendritic cells. The latter are the first cells to recognize antigens. Sirolimus blocks the growth of dendritic cells and a number of other cells, such as tumors and endothelial cells, which are activated by the tumor cell releasing vascular endothelial growth factor (VEGF). VEGF is a central regulator of angiogenesis (formation of new blood vessels from pre-existing vessels) and vasculogenesis (development of embryonic vasculature through an influence on endothelial cell differentiation and organization). Diseases that are characterized by abnormal angiogenesis and vasculogenesis, such as some cancers and some ocular diseases, may show abnormal production of VEGF. Thus, control of VEGF function may be one means to control or treat these diseases. Sirolimus has also been used in the prevention of smooth muscle hyperplasia after coronary stent surgery. The use of sirolimus and ascomycin as specific medicaments for treatment of ocular disease has been disclosed in co-pending U.S. patent application Ser. No. 10/631,143.

Everolimus, also known as RAD-001, SCZ RAD, Certican® (Novartis, Basel Switzerland), is an analog of sirolimus but is a new and distinct chemical entity. It is an oral immunosuppressant that inhibits growth factor-induced cell proliferation and thus reduces acute organ rejection and vasculopathy, the proliferation of smooth muscle cells in the innermost wall of grafts that restricts blood supply.

It will be appreciated that the invention encompasses the use of macrolides in addition to those previously described. These include, for example, clindamycin, leucomycins, zoatrolimus, the known antibiotics erythromycin and its derivatives such as azithromycin and clarithromycin, lincomycin, dirithromycin, josamycin, spiramycin, diacetyl-midecamycin, troleandomycin, tylosin, and roxithromycin, and other macrolides such as biolimus, ABT-578 (methylrapamycin); macrolide derivatives such as temsirolimus (CCI-779, Wyeth) and AP23573 (Ariad) (both rapamycin derivatives). The invention also includes new macrolide antibiotic scaffolds and derivatives in development, including but not limited to the ketolides ABT-773 and telithromycin as described by Schonfeld and Kirst (Eds.) in Macrolide Antibiotics, Birkhauser, Basel Switzerland (2002); macrolides derived from leucomycins, as described in U.S. Pat. Nos. 6,436,906; 6,440,942; and 6,462,026 assigned to Enanta Pharmaceuticals (Watertown Mass.); and lincosamides, each of which is incorporated by reference herein.

Any of the above-described macrolides may be used in the invention. In one embodiment, the total macrolide concentration ranges from less than 1 ng/ml to about 10 mg/ml. In another embodiment, the total macrolide concentration ranges from about 1 ng/ml to about 1 mg/ml. In another embodiment, the total macrolide concentration ranges from about 20 μg/ml to about 200 μg/m. In another embodiment, the total macrolide concentration is below 5 mg/ml. Formulations and doses of macrolides are described in U.S. patent application Ser. Nos. 10/667,161 and 10,/752/124, each of which is expressly incorporated by reference herein in its entirety.

Specific macrolide analogues accelerate nerve regeneration and functional recovery, as disclosed in Revill et al., J. Pharmacol. Exp. Therap. (2002) 302; 1278, which is expressly incorporated by reference herein in its entirety. For example, genetically engineered 13- and 15-desmethoxy analogs of ascomycin, examples of macrolide analogs, that contain hydrogen, methyl, or ethyl instead of methoxy at either the 13-, the 15-, or both the 13- and 15-positions, enhanced neurite outgrowth in cultured SH-SY5Y neuroblastoma cells at concentrations of 1 mg/kg/day and 5 mg/kg/day, with nerve growth factor (NGF) at a concentration of 10 ng/ml. The ascomycin analog 13-desmethoxy-13-methyl-18 hydroxy (13-Me-18-OH), at concentrations of 1 mg/kg/day and 5 mg/kg/day, was demonstrated to accelerate nerve regeneration and lead to full functional recovery (walking) in a rat sciatic nerve crush model.

The combination of a macrolide and another neurostimulatory or neuroprotective factor(s) such as neurotrophins or neuropoietins is used in one embodiment.

Neurotrophins are a family of polypeptides that enhance survival of nervous tissue by maintenance, growth, differentiation, etc. They stimulate the growth of sympathetic and sensory nerve cells in both the central and peripheral nervous system. All neurotrophins have six conserved cysteine residues and share a 55% amino acid sequence identity. Some are in a pro-neurotrophin form and are cleaved to produce a mature form. Examples of neurotrophins include nerve growth factor-β (NGFβ), brain-derived neurotrophic factor (BDNF), neurotrophin 3 (NT-3), neurotrophin 4 (NT-4), neurotrophin 6 (NT-6). These are available commercially, for example, from Sigma-Aldrich (St. Louis Mo.); Axxora (San Diego Calif.) mouse 2.5S and 7S components NGFβ, human recombinant β-NGF and pro-β-NGF. Further examples of neurotrophins are products of the neural regeneration protein (NRP) gene.

Different neuron types require different neurotrophins, depending upon their receptor expression. All neurotrophins are capable of binding to p75 neurotrophin growth factor receptors, which are low affinity receptors. Specific neurotrophins and mature neurotrophins bind to different tyrosine kinase (trk) receptors, which are higher affinity receptors than p75 receptors. Tyrosine kinase receptors include types A (trkA), B (trkB), and C (trkC).

NGFβ is a specific ligand for the trkA receptor and signals through trkA. It also signals through the low affinity p75 receptors. NGFβ is a secreted protein that helps to develop and maintain the sympathetic nervous system, affecting sensory, pain, and sympathetic targets. It is required for survival of small, peptide-expressing neurons that express the trkA receptor and that project into the superficial laminae of the dorsal horn (i.e., putative nociceptive neurons).

BDNF signals through trkB, in addition to the low affinity p75 receptors. It is $Ca^{2+}$ dependent and may control synaptic transmission and long term synaptic plasticity, affecting sensory and motor targets. It enhances survival and differentiation of several classes of neurons in vitro, including neural crest and placode-derived sensory neurons, dopaminergic neurons in the substantia nigra, basal forebrain cholinergic neurons, hippocampal neurons, and retinal ganglial cells. BDNF is expressed within peripheral ganglia and is not restricted to neuronal target fields, so that it may have paracrine or autocrine actions on neurons as well as non-neuronal cells.

Neurotrophin-3 (NT-3) is part of the family of neurotrophic factors that control survival and differentiation of mammalian neurons. NT-3 is closely related to NGFβ and BDNF. The mature NT-3 peptide is identical in all mammals examined including human, pig, rat and mouse. NT-3 preferentially signals through trkC, over trkA and trkB receptors, and also utilizes the low affinity p75 receptors. It functions at the neuromuscular junction, affecting large sensory and motor targets and regulating neurotransmitter release at neuromuscular synapses. It may be involved in maintenance of the adult nervous system, and affect development of neurons in the embryo when it is expressed in human placenta.

Neurotrophin 4 (NT-4, synonymous with NT-5) belongs to the NGF-β family and is a survival factor for peripheral sensory sympathetic neurons. NT-4 levels are highest in the prostate, with lower levels in thymus, placenta, and skeletal muscle. NT-4 is also expressed in embryonic and adult tissues. It signals through trkB in addition to low affinity p75 receptors, affecting sympathetic, sensory, and motor targets. Neurotrophin-6 has also been reported.

Ciliary neurotrophic factor (CNTF) is expressed in glial cells within the central and peripheral nervous systems. It stimulates gene expression, cell survival, or differentiation in a variety of neuronal cell types such as sensory, sympathetic, ciliary, and motor neurons. CNTF itself lacks a classical signal peptide sequence of a secreted protein, but is thought to convey its cytoprotective effects after release from adult glial cells by some mechanism induced by injury. In addition to its neuronal actions, CNTF also acts on non-neuronal cells such as glia, hepatocytes, skeletal muscle, embryonic stem cells, and bone marrow stromal cells.

Glial cell derived neurotrophic factor (GDNF) is a 20 kD glycosylated polypeptide that exists as a homodimer. It stimulates the growth of dopaminergic neurons and autonomic motor neurons.

Neuropoietic factors may be used in addition to, or in place of, neurotrophic factors. Neuropoietic factors regulate the properties of cells both in the peripheral and central nervous systems, and both during development and in the mature nervous system. They regulate neuronal phenotype (neurotransmitter) and differentiation of neuronal precursor cells in peripheral and spinal cord neurons. They also regulate cell survival, and development of astrocytes and oligodendrocytes. Neuropoietic factors are also trauma factors in rescuing sensory and motor neurons from axotomy-induced cell death. They show temporal and spatial specific expression patterns, and have specific roles in neural development and repair.

Neuropoietic factors include some cytokines, different from cytokines associated with apoptosis-induced neurodegenerative processes, and hematopoietic factors that fulfill criteria for demonstrating a role in neuronal differentiation and survival. They include leukemia inhibitory factor (LIF), oncostatin M, growth-promoting activity, and cardiotrophin 1. All of these factors activate a subfamily of class I cytokine receptors, the interleukin-6 receptor family.

Any of the above-described neurotrophins and/or neuropoietic factors may be used in the invention. In one embodiment, the total concentration of neurotrophins and/or neuropoietic factors ranges from about 1 pM to about 100 pM. In another embodiment, the total concentration of neurotrophins and/or neuropoietic factors ranges from about 0.01 nM to about 1 M. In another embodiment, the total concentration of neurotrophins and/or neuropoietic factors is below 1 nM. The neurotrophin(s) and/or neuropoietic factor(s) may be used singly or in combination.

The addition of a macrolide, macrolide analog, neurotrophin and/or a neuropoietic factor, alone or in combination, in an ocular formulation, provides beneficial results in enhancing corneal sensation, nerve regeneration, protection, and/or re-enervation. In embodiments where a macrolide is present, the composition also reduces post ocular surgical scarring, provides anti-inflammatory effects, and may provide anti-infective properties. It will be appreciated that various embodiments are contemplated. As one example, a macrolide or macrolide analog, with or without neurostimulatory activity, may be used without a neurotrophin or neuropoietic factor. As another example, a neurotrophin or neuropoietic factor or any other neuro-stimulatory factor or factors may be used alone. As another example, other agents may be included in the composition. Examples of these agents include, but are not limited to, steroids, non-steroidal anti-inflammatory agents (NSAIDS), antibiotics, antioxidants, anti-proliferative, anti-cell migration, and/or anti-angiogenic agents.

Steroids for ocular administration include, but are not limited to, triamcinolone (Aristocort®; Kenalog®), betamethasone (Celestone®), budesonide, cortisone, dexamethasone (Decadron-LA®; Decadron® phosphate; Maxidex® and Tobradex® (Alcon)), hydrocortisone, methylprednisolone (Depo-Medrol®, Solu-Medrol®), prednisolone (prednisolone acetate, e.g., Pred Forte® (Allergan); Econopred and Econopred Plus® (Alcon); AK-Tate® (Akorn); Pred Mild® (Allergan); prednisone sodium phosphate (Inflamase Mild and Inflamase Forte® (Ciba); Metreton® (Schering); AK-Pred® (Akorn)), fluorometholone (fluorometholone acetate (Flarex® (Alcon); Eflone®), fluorometholone alcohol (FML® and FML-Mild®, (Allergan); FluorOP®)), rimexolone (Vexol® (Alcon)), medrysone alcohol (HMS® (Allergan)); lotoprednol etabonate (Lotemax® and Alrex® (Bausch & Lomb), 11-desoxcortisol, and anacortave acetate (Alcon)).

Antibiotics include, but are not limited to, doxycycline (4-(dimethylamino)-1,4,4a,5,5a,6,11,12a-octahydro-3,5,10, 12,12a-pentahydroxy-6-methyl-1, 11-dioxo-2-naphthacenecarboxamide monohydrate, $C_{22}H_{24}N_2O_8 \cdot H_2O$), aminoglycosides (e.g., streptomycin, amikacin, gentamicin, tobramycin), cephalosporins (e.g., beta lactams including penicillin), tetracyclines, acyclorvir, amantadine, polymyxin B, amphtotericin B, amoxicillin, ampicillin, atovaquone, azithromycin, azithromycin, bacitracin, cefazolin, cefepime, cefotaxime, cefotetan, cefpodoxime, ceftazidime, ceftizoxime, ceftriaxone, cefuroxime, cephalexin, chloramphenicol, clotimazole, ciprofloxacin, clarithromycin, clindamycin, dapsone, dicloxacillin, erythromycin, fluconazole, foscarnet, ganciclovir, gatifloxacin, griseofulvin, isoniazid, itraconazole, ketoconazole, metronidazole, nafcillin, neomycin, nitrofurantoin, nystatin, pentamidine, rifampin, rifamycin, valacyclovir, vancomycin, etc.

Anti-proliferative agents include, but are not limited to, carboplatin, 5-fluorouracil (5-FU), thiotepa, etoposide (VP-16), doxorubicin, ifosphophamide, cyclophosphamide, etc.

Anti-prostaglandins include, but are not limited to, indomethacin, ketorolac tromethamine 0.5% ((±)-5-benzoyl-2,3-dihydro-1H-pyrrolizine-1-carboxylic acid, compound with 2-amino-2-(hydroxymethyl)-1,3-propanediol (1:1) (ACULAR® Allegan, Irvine Calif.), OCUFEN® (flurbiprofen sodium 0.03%), meclofenamate, fluorbiprofen, and compounds in the pyrrolo-pyrrole group of non-steroidal anti-inflammatory drugs.

A matrix metalloproteinase inhibitor may be added. These include, but are not limited to, doxycycline, TIMP-1, TIMP-2, TIMP-3, TIMP-4, MMP1, MMP2, MMP3, Batimastat, or marimastat. Eight matrix metalloproteinase inhibitors have been identified in the cornea, namely, collagenases I and III (MMP-1 and MMP-13), gelatinases A and B (MMP-2 and MMP-9), stromelysin (MMP-3), matrilysin (MMP-7), and membrane type MMP (MMP-14).

Anti-angiogenesis agents include, but are not limited to, antibodies to vascular endothelial growth factor (VEGF) such as bevacizumab (AVASTIN®) and rhuFAb V2 (ranibizumab) (Genentech), and other anti-VEGF compounds; MACUGEN® (pegaptanim sodium, anti-VEGF aptamer or EYE001) (Eyetech Pharmaceuticals), pigment epithelium derived factor(s) (PEDF); CELEBREX®; VIOXX®; interferon alpha; interleukin-12 (IL-12); thalidomide and derivatives such as REVIMID™ (CC-5013) (Celgene Corporation); squalamine; endostatin; angiostatin; the ribozyme inhibitor ANGIOZYME® (Sirna Therapeutics); multifunctional antiangiogenic agents such as NEOVASTAT® (AE-941) (Aeterna Laboratories, Quebec City, Canada); etc., as known to one skilled in the art.

Other agents may also be added, such as NSAIDS, vitamins, minerals, cytokines, growth factors, etc. Examples of the above include, but are not limited to, colchicine, naproxen sodium (ANAPROX® and ANAPROX DS®, (Roche); flurbiprofen (ANSAID®, Pharmacia Pfizer); diclofenac sodium and misoprostil (ARTHROTEC®, Searle Monsanto); valdecoxib (BEXTRA®, Pfizer); diclofenac potassium (CATAFLAM®, Novartis); celecoxib (CELEBREX®, Searle Monsanto); sulindac (CLINORIL®, Merck); oxaprozin (DAYPRO®, Pharmacia Pfizer); salsalate (DISALCID®, 3M); salicylate (DOLOBID®, Merck); naproxen sodium (EC NAPROSYN®, Roche); piroxicam (FELDENE®, Pfizer); indomethacin (INDOCIN®, Merck); etodolac (LODINE®, Wyeth); meloxicam (MOBIC®, Boehringer Ingelheim); ibuprofen (MOTRIN®, Pharmacia Pfizer); naproxen (NAPRELAN®, Elan); naproxen (NAPROSYN®, Roche); ketoprofen (ORUDIS®, ORUVAIL®, Wyeth); nabumetone (RELAFEN®, SmithKline); tolmetin sodium (TOLECTIN®, McNeil); choline magnesium trisalicylate (TRILISATE®, Purdue Fredrick); rofecoxib (VIOXX®, Merck), vitamins A, B (thiamine), $B_6$ (pyridoxine), $B_{12}$ (cobalamine), C (ascorbic acid), $D_1$, $D_2$ (ergocalciferol), $D_3$ (cholcalciferol), E, K (phytonadione), $K_1$ (phytylmenaquinone), $K_2$ (multiprenylmenaquinone); carotenoids such as lutein and zeaxanthin; macrominerals and trace minerals including, but not limited to, calcium, magnesium, iron, iodine, zinc, copper, chromium, selenium, manganese, molybdenum, fluoride, boron, etc. Commercially available supplements are also included such as high potency zinc (commercially available as OCUVITE® PRESERVISION®, Bausch & Lomb, Rochester N.Y.), or high potency antioxidants (zinc, lutein, zeaxanthin) (commercially available as ICAPS® Dietary Supplement, Alcon, Fort Worth Tex.).

It will be appreciated that the above agents include pharmaceutically acceptable salts and derivatives (e.g., sodium, potassium bicarbonate, sulfate, etc.), and are representative but not exclusive. The duration over which any of the formulation will dwell in the ocular environment will depend on factors that include, but are not limited to, compound(s) pharmacological properties, concentrations, and/or bioavailability, disease, mode of administration, desired longevity of therapy, etc. Formulations of embodiment may have dwell times of hours, days, weeks, months, or years.

In one example, rabbits are administered neurostimulatory or neuroprotective macrolides, macrolide analogs, neurotrophins, and/or neuropoietic factors (treated) or vehicle alone (control). To generate damage to retinal sensory or ganglion cells, anesthetized rabbits may be subjected to a sever crush injury of the optic nerve, or may be treated to induce increased intraocular pressure, or may be treated to induce retinal ischemic/reperfusion injury, or may be subject to other methods known to one skilled in the art.

As an example of one embodiment, after excising the conjunctiva and exposing the optic nerve with the aid of a binocular operating microscope with care not to interfere with the blood supply, the nerve can be mechanically crushed for a defined period using forceps or other instruments, as described in Schori et al., PNAS 98:3398(2001), which is expressly incorporated by reference herein in its entirety.

As an example of another embodiment, rabbits may be treated to result in intraocular pressure greater than 17 mm Hg. This may be done by negative pressure applied to a corneoscleral ring fixed to the sclera and connected to a vacuum source, as known to one skilled in the art. This may also be done by positive pressure applied through a cannula connected to the interior chamber. This may also be done by blocking aqueous outflow using 80-120 applications of blue-green argon laser as described in Bakalash et al., Investigative Ophthalmology & Visual Science 44: 3374 (2003), which is expressly incorporated by reference herein.

As an example of another embodiment, the central and choroidal arteries may be surgically closed. Deprivation of blood flow to the retina would result in ischemia due to lack of oxygen and nutrients, while reperfusion would result in free radical injury; this type of ischemia/reperfusion injury is known to one skilled in the art.

One or a combination of the macrolides, macrolide analogues, neurotrophins, and neuropoietic factors in different combinations of agent, dose, route of administration, intervals, etc. as described herein may be used and administered as previously described.

Assessment of retinal damage in control and treated animals may be by applying dextran tetramethylrhodamine, a hydrophilic neurotracer (Molecular Probes, Eugene Oreg.) into the intraorbital portion of the optic nerve, with only functional axons capable of dye uptake. Rabbits are sacrificed twenty-four hours after dye administration, retinas excised, wholemounted, and preserved in 4% paraformaldehyde. Retinal ganglial cells are counted under 800× magnification using a fluorescence microscope. Four fields from each retina are counted with the same diameter and located the same distance from the optic disc. Eyes from untreated rabbits are used as controls.

Other dyes or markers for viable ganglion cells can be introduced and the number of cells can be counted in treated groups versus control groups. In addition, factors other than dye uptake can be used as an indicator of neuroprotection and/or neurostimulation. These factors include retinal ganglial and/or sensory cell morphology from treated versus control groups, assays of cellular function, conductivity, etc. Conversely, apoptosis may be assayed in retinal ganglial and/or sensory cells from treated versus control groups. For example, Annexin V binding is known by one skilled in the art as an indirect indicator of apoptosis, and binding can be assayed in treated versus control cells. A clonagenic assay is known by one skilled in the art as a direct indicator of apoptosis, and can be performed with the results compared from both treated and control cells.

It will be appreciated that the agents include pharmaceutically acceptable salts and derivatives thereof (e.g., sodium, potassium, bicarbonate, sulfate, etc). It will also be appreciated that the above lists are representative only and are not exclusive. The indications, effective doses, formulations (including buffers, salts, and other excipients), contraindications, vendors, etc. of each of the above are known to one skilled in the art.

In one embodiment, the composition is formulated for topical application. In another embodiment, the composition is formulated for intraocular application. In another embodiment, the composition is formulated for subconjunctival or intravitreal application. In another embodiment, the composition is in a delayed- or extend-release formulation. In another embodiment, the composition is formulated on or in an intraocular lens (e.g., implanted lens, contact lens). In another embodiment, the composition is formulated on or in an implanted ocular device. None of these formulations result in significant systemic absorption, so that there are no detrimental effects that may result with systemically administered macrolides and/or neurostimulatory factor(s).

The formulation may be a slow, extended, or time release formulation, a carrier formulation such as microspheres, microcapsules, liposomes, etc., as known to one skilled in the art. Any of the above-mentioned delayed release delivery systems may be administered topically, intraocularly, sub-conjunctivally, or by implant to result in sustained release of the agent over a period of time. The formulation may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety, or lipids that may be formulated as microspheres or liposomes. A microscopic or macroscopic formulation may be administered topically or through a needle, or may be implanted. Delayed or extended release properties may be provided through various formulations of the vehicle (coated or uncoated microsphere, coated or uncoated capsule, lipid or polymer components, unilamellar or multilamellar structure, and combinations of the above, etc.). The formulation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety. For example, a sustained release intraocular implant may be inserted through the pars plana for implantation in the vitreous cavity. An intraocular injection may be into the vitreous (intravitreal), or under the conjunctiva (subconjunctival), or behind the eye (retrobulbar), or under the Capsule of Tenon (sub-Tenon), and may be in a depot form. The composition may be administered via a contact lens applied to the exterior surface of an eye, with the composition incorporated into the lens material (e.g., at manufacture, or contained in a lens solution). The composition may be administered via an intraocular lens (IOL) that is implanted in the eye. Implantable lenses include any IOL used to replace a patient's diseased lens following cataract surgery, including but not limited to those manufactured by Bausch and Lomb (Rochester N.Y.), Alcon (Fort Worth Tex.), Allergan (Irvine Calif.), and Advanced Medical Optics (Santa Ana Calif.). When the lens is implanted within the lens capsule, the composition provides the desired effect to the eye. Concentrations suitable for implants (lenses and other types) and by contact lens administration may vary, as will be appreciated by one skilled in the art. For example, an implant may be loaded with a high amount of agent, but formulated or regulated so that a required concentration within the above-described ranges is sustainedly released (e.g., slow release formulation).

In various embodiments, the composition is administered up to four times a day. In embodiments where the composition is administered after surgery, administration may commence following surgery on the same day, or the day after surgery, or a few days after surgery, or any time after surgery. The composition may be self-administered or administered by another, for example, if visual acuity is poor, or if the patient is uncomfortable with self-administration. The patient is periodically evaluated (e.g., daily, every other day, etc.) using assessment methods known to one skilled in the art. In embodiments where the composition is used to assess corneal sensation, these include assessment of corneal clarity, corneal sensation (e.g., using a Cochet-Bonnet filament-type aesthesiometer), corneal enervation, etc. In embodiments where the composition is used to enhance ocular neuroprotection and/or neurostimulation, these may include one or more of the following assessments: retinal ganglial cell viability, quantitation of ocular glutamate levels, visual field and visual acuity determinations, assessment of visual evoked potential (VEP) to evaluate visual neural pathways via electrode measurement of brain electrical activity while watching a moving pattern on a video monitor, electroretinogram (ERG) to evaluate the ocular electrical responses to a flash of light using an electrode placed on the surface of the eye (e.g., cornea), electrooculargram (EOG), critical flicker fusion (CFF) test that measures a sensitivity threshold to provide information about the temporal responsiveness of visual pathways, etc. These assessments are known to one skilled in the art.

The following examples provide further embodiments of the invention.

EXAMPLE 1

LASIK surgery was performed on each eye of twenty-two patients. Each patient was enrolled in a single-center clinical trial.

In this surgery, corneal nerves in the hinge region remained unaffected (i.e., they remained both present and intact). Corneal nerves in the remainder of the flap, however, were mechanically dissected during surgery to mobilize the flap, but remained structurally present (i.e., they remained present but not intact).

It is known that after this type of surgery, nerves that have been severed gradually and over the course of months reenervate the cornea. Corneal sensation is thus gradually restored at a slow rate during normal post-surgical recovery.

The rate of corneal sensation restoration by a commercially available 0.05% cyclosporine emulsion applied to an eye after LASIK surgery was assessed. Twenty-two patients underwent LASIK surgery using a combined Excimer laser with a lamellar corneal flap technique, as known to one skilled the art and as discussed in, e.g., Linna et al., Exp. Eye Res. (1998) 66, 755, which is expressly incorporated by reference herein. One eye was randomly assigned as a "study" eye, and the other eye was the "control" eye. The surgeon was instructed to ensure that the hinge position of the LASIK flap was the same for both eyes of the patient, because this affected corneal sensation in that the loss of corneal sensation was known to be greater in eyes with a superior-hinge flap than in eyes with a nasal-hinge flap.

At the completion of the LASIK surgery, one drop of cyclosporine 0.05% ophthalmic emulsion was topically applied to one eye ("study eye") of the patient. After at least ten minutes, one drop of each of prednisolone acetate (ECONOPRED® Alcon, Ft. Worth Tex.) and moxifloxacin (VIGAMOX®. Alcon) were topically applied to the same "study" eye. One drop of each of prednisolone acetate and moxifloxacin were topically applied to the "control" eye of the same patient. Cyclosporine was not applied to the "control" eye.

Patients were instructed to administer the following medicaments to the "study" eye, starting on the day of surgery: one drop of cyclosporine 0.05% at about twelve hour intervals, and one drop of each of prednisolone acetate and moxifloxacin four times a day, waiting at least ten minutes after cyclosporine administration. Patients were instructed to administer the following medicaments to the "control" eye, starting on the day of surgery: one drop of each of prednisolone acetate and moxifloxacin four times a day, The cyclosporine administration regimen to the "study" eye continued until the three month post-surgical evaluation. The prednisolone acetate and moxifloxacin regimen administration to the "study" eye continued until a one-week post-surgical evaluation, then changed to twice a day administration for two days, then once a day for two days. An ocular lubricant (SYSTANE® Alcon) was administered to both "study" and "control" eyes once on the day of surgery, and thereafter as needed.

Patients were evaluated for corneal sensitivity pre-surgery and immediately post-surgery, then at one- and three-months post-surgery. Nineteen patients (thirty-eight eyes) were evaluated at the three-month examination; the remaining patients did not report. Post-surgical corneal sensitivity recovery of the 19 study eyes and 19 control eyes was compared.

Corneal sensitivity was measured using the Cochet-Bonnet esthesiometer in accord with the manufacturer's instructions. The instrument is a nylon filament 60.0 mm long and 0.12 mm diameter. The force exerted by the filament when it touches the cornea is inversely proportional to its length. The same experienced examiner made all measurements whenever possible.

Measurements were obtained at nine different areas of the cornea, as diagrammed in FIG. 1, also showing location of the surgically created corneal flap where the continuous line shows the hinge of the flap that is attached to the rest of the cornea, and the dashed line shows the extent of the flap. As shown in FIG. 1, corneal sensitivity measurements were taken at the four quadrants of untreated cornea (areas 1, 2, 8, and 9), the four peripheral quadrants of the flap (areas 3, 4, 6, and 7), and the center of the flap (area 5).

For post-surgical examination, the examiner was unaware of which patient eye was the "study" eye and which eye was the "control" eye. The patient, in a supine position looking straight ahead, was asked to indicate to the examiner when the stimulus was felt (positive response). The filament was moved toward the cornea smoothly at a perpendicular angle, guided by its corneal reflex. Contact was detected by a slight bending in the filament. If the patient did not respond to the first contact, the length of the filament was decreased by 5.0 mm, and the procedure was repeated until the patient reported feeling corneal contact. The longest filament length at which a minimum of three stimulus applications produced a positive response from the patient was recorded. This was considered the corneal touch threshold.

Data were statistically evaluated using the Wilcoxon Sum Rank Test. Statistical significance of differences in corneal sensitivity was determined by comparing the two eyes of each patient (one study eye and one control eye in each patient), using statistical significance at $p = 0.05$.

Figure 2A:
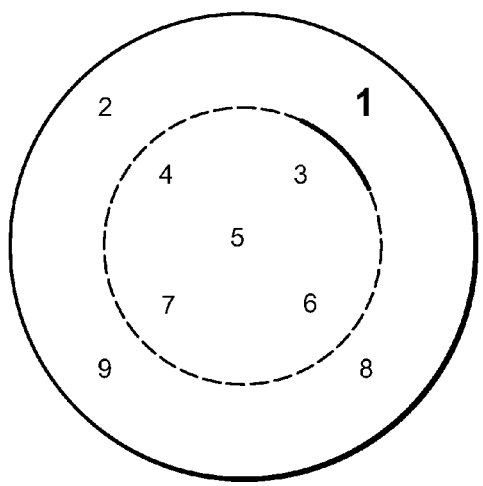
FIGS. 2A and 2B show pre- and post-surgical corneal sensitivity data from area 1.
Figure 2B:
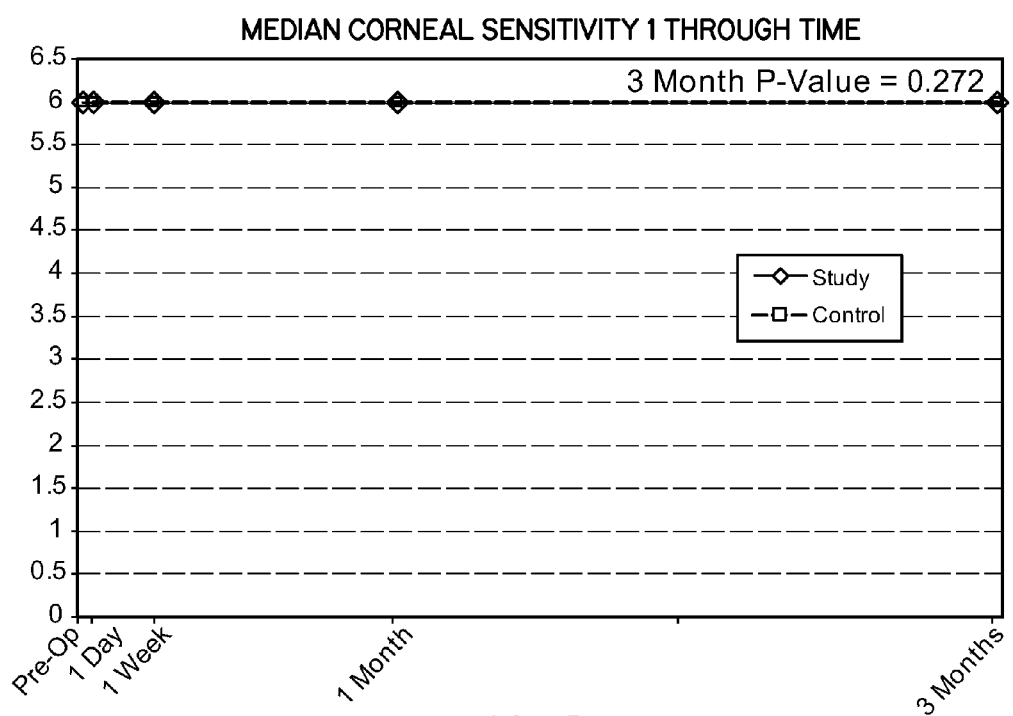
Figure 3A:
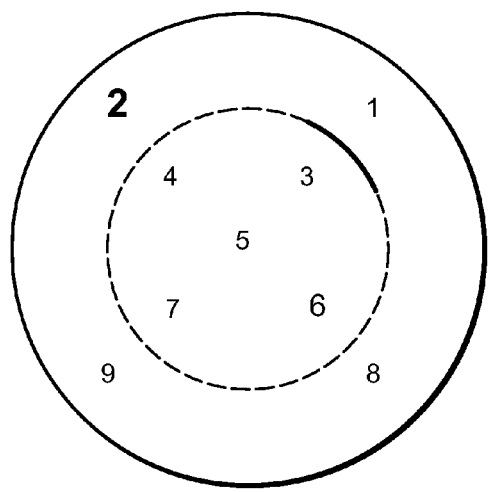
FIGS. 3A and 3B show pre- and post-surgical corneal sensitivity data from area 2.
Figure 3B:
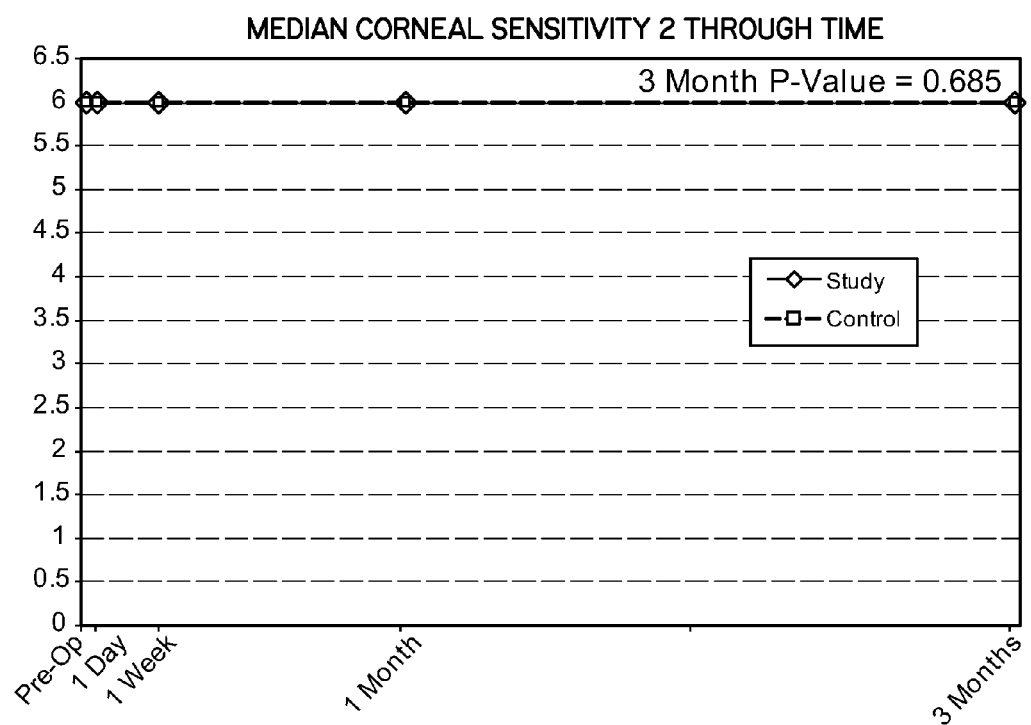
Figure 4A:
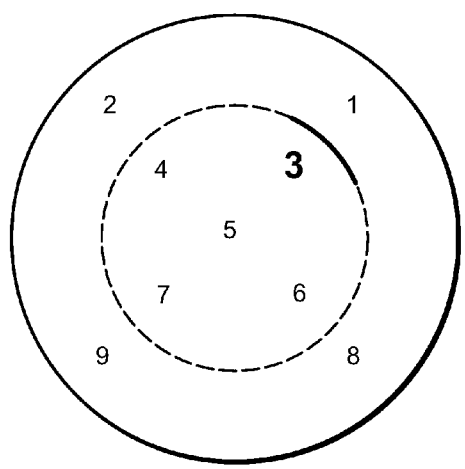
FIGS. 4A and 4B show pre- and post-surgical corneal sensitivity data from area 3.
Figure 4B:
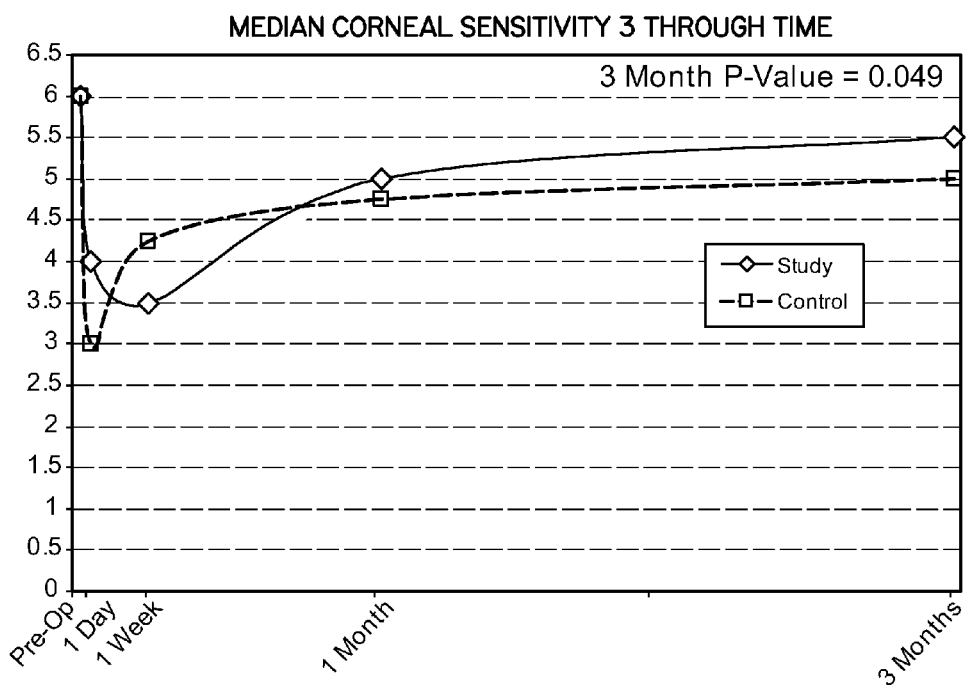
Figure 5A:
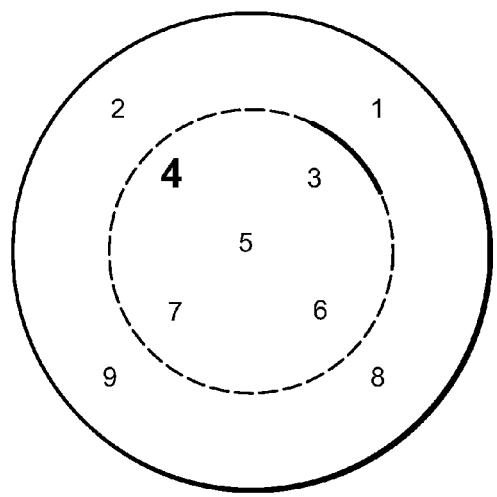
FIGS. 5A and 5B show pre- and post-surgical corneal sensitivity data from area 4.
Figure 5B:
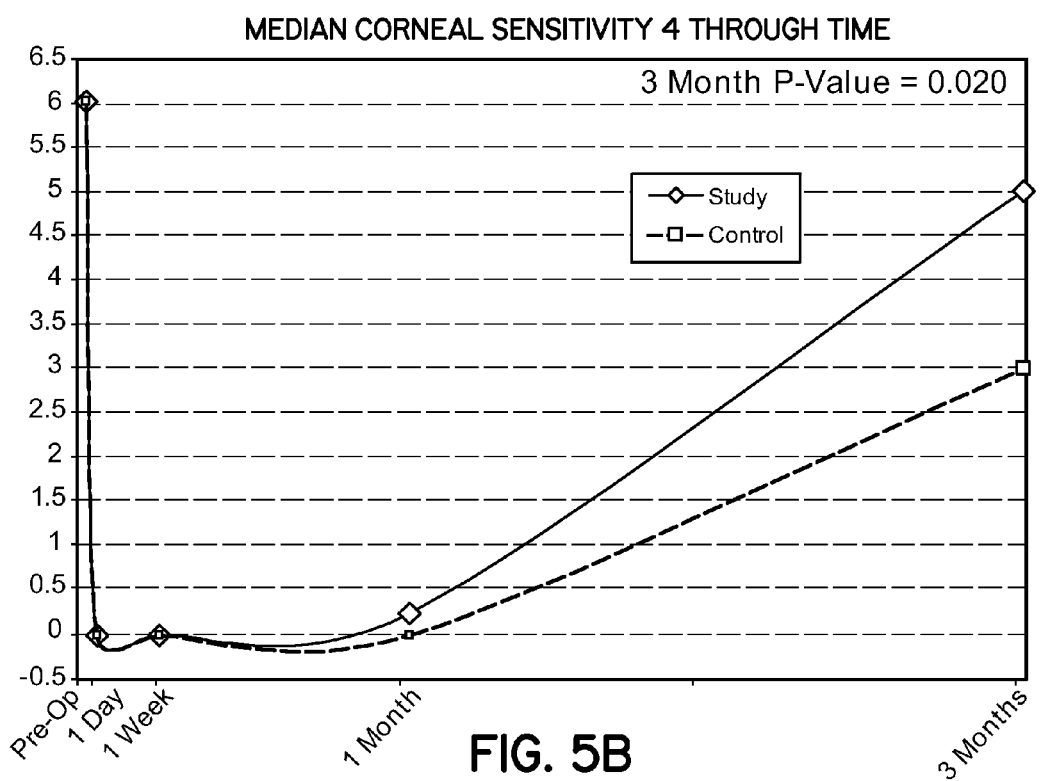
Figure 6A:
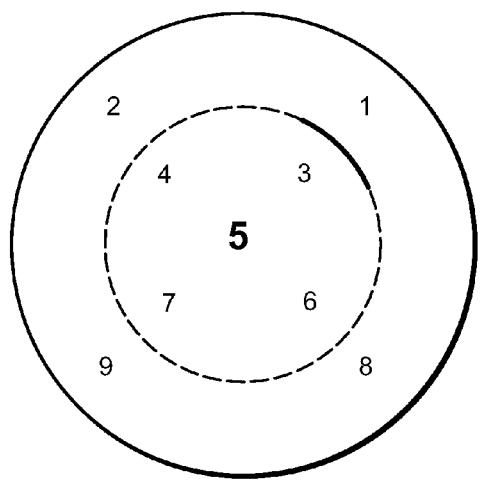
FIGS. 6A and 6B show pre- and post-surgical corneal sensitivity data from area 5.
Figure 6B:
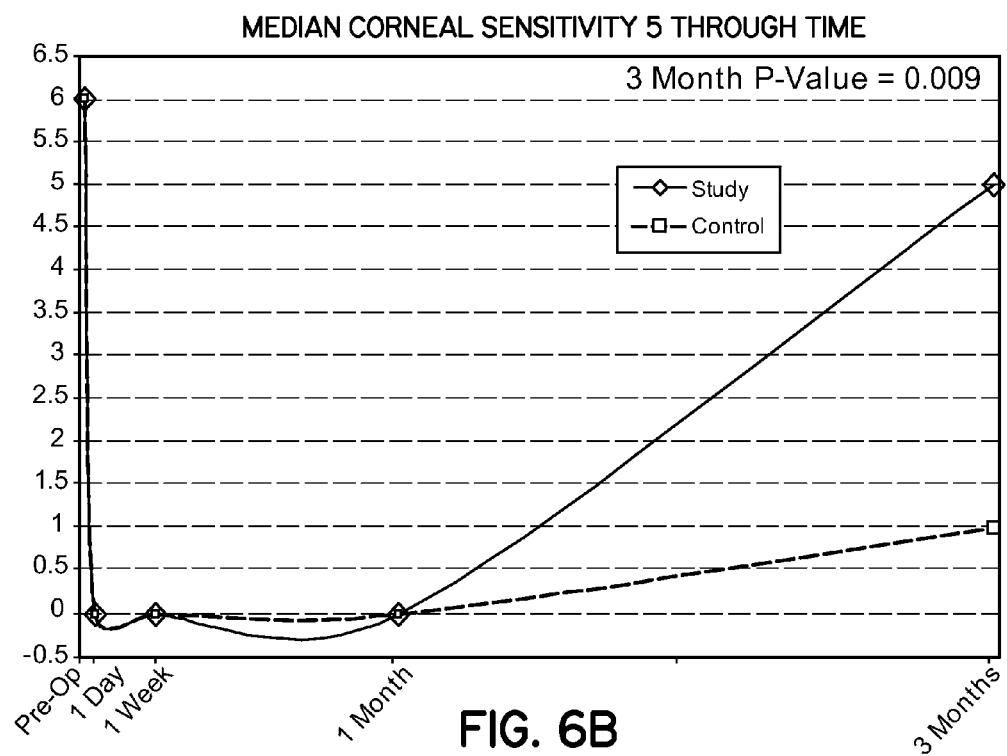
Figure 7A:
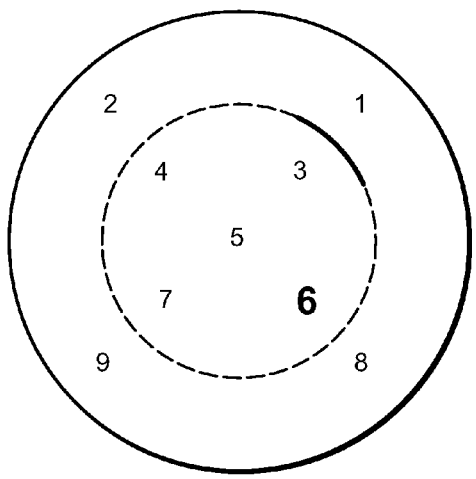
FIGS. 7A and 7B show pre- and post-surgical corneal sensitivity data from area 6.
Figure 7B:
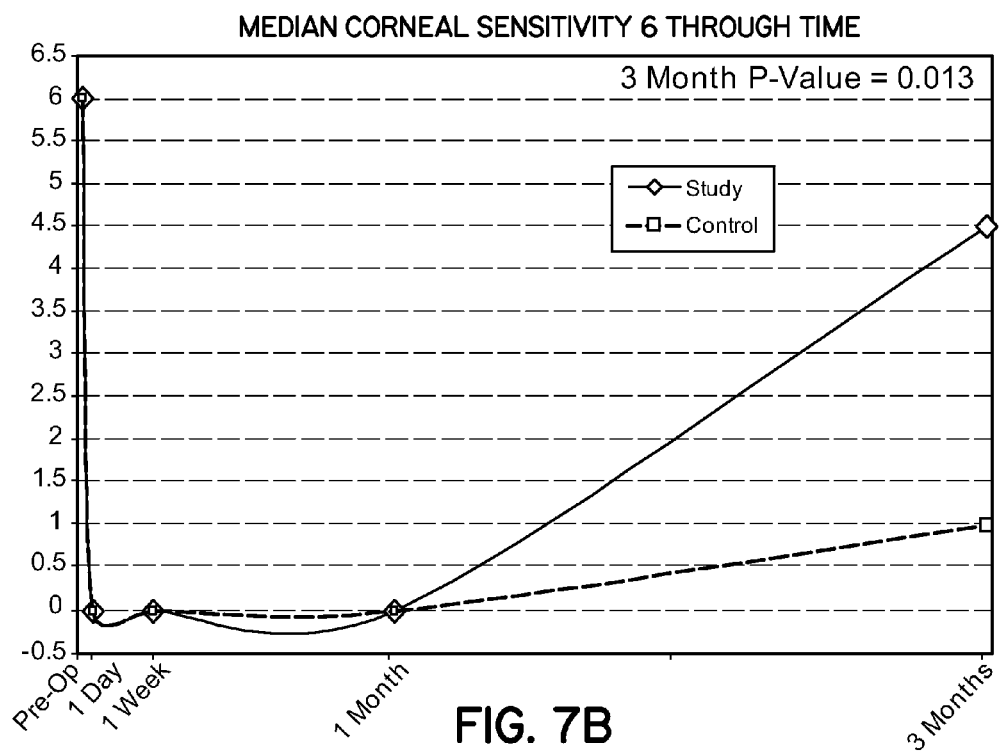
Figure 8A:
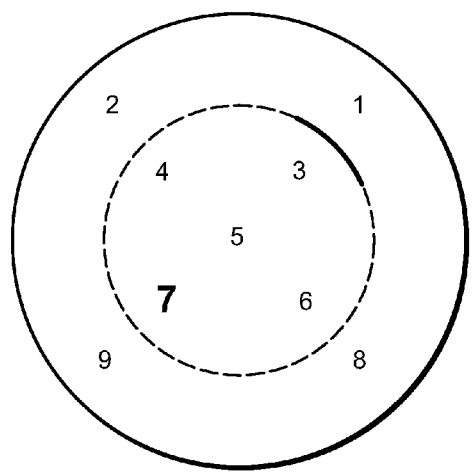
FIGS. 8A and 8B show pre- and post-surgical corneal sensitivity data from area 7.
Figure 8B:
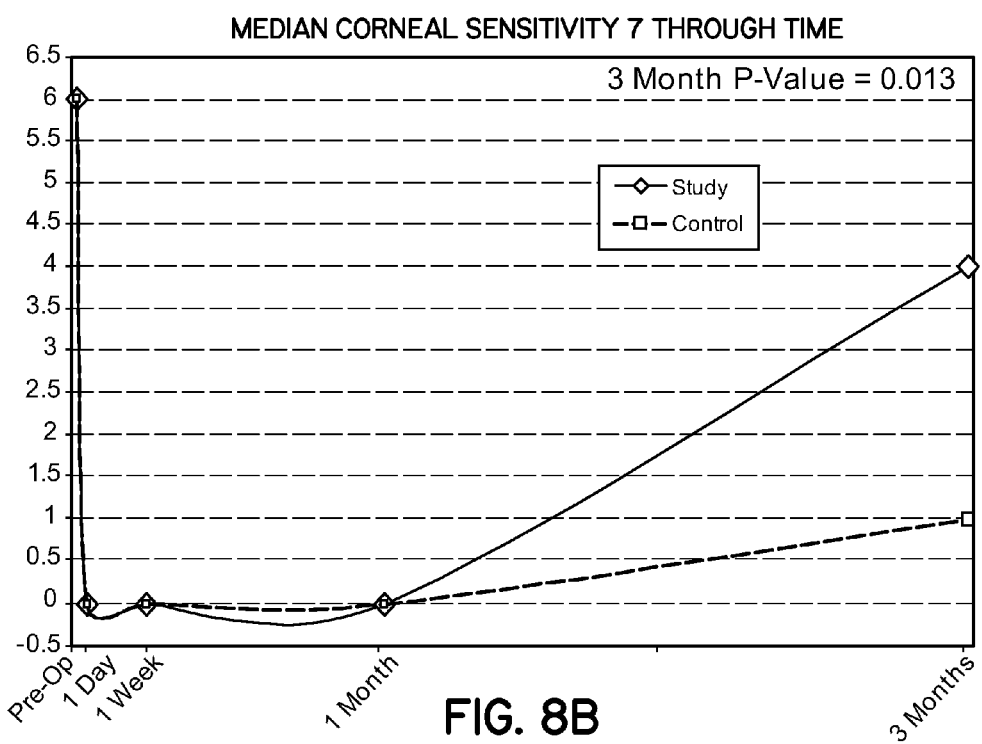
Figure 9A:
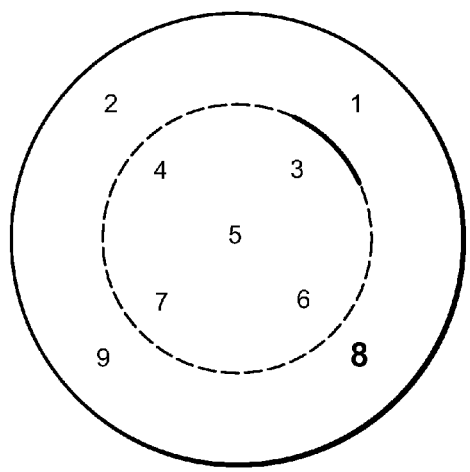
FIGS. 9A and 9B show pre- and post-surgical corneal sensitivity data from area 8.
Figure 9B:
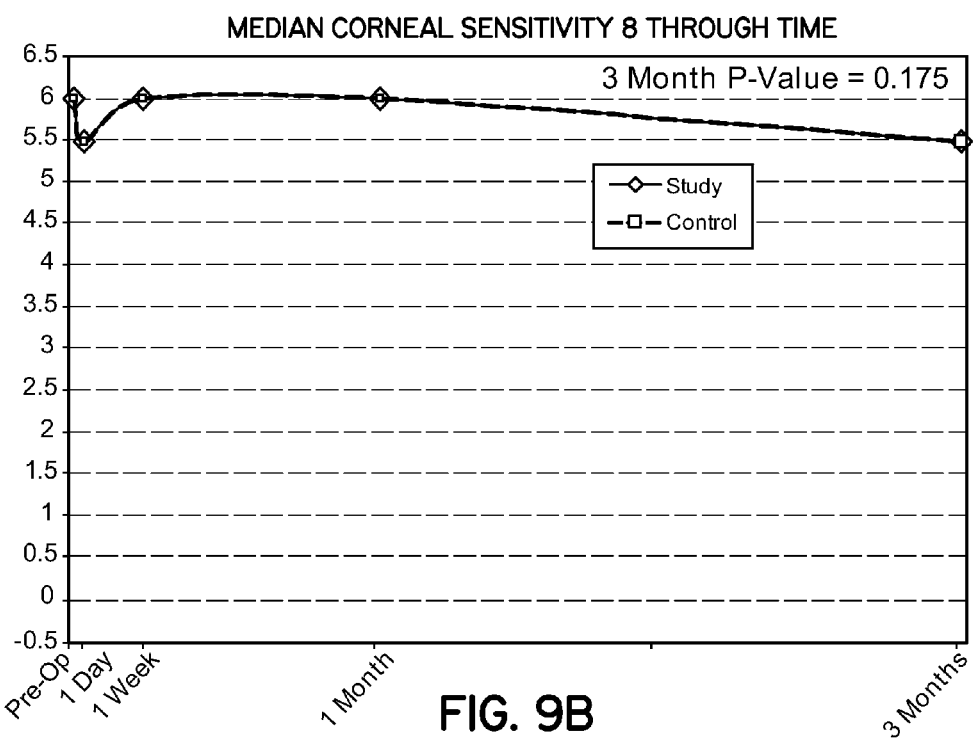
Figure 10A:
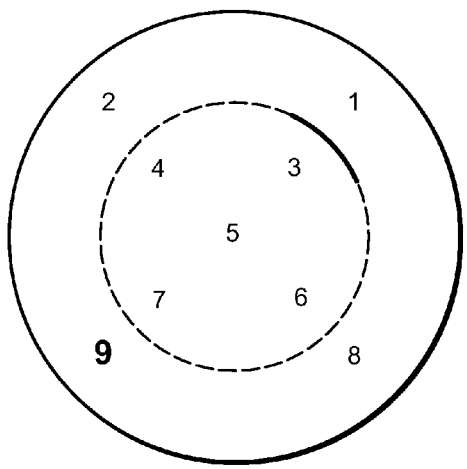
FIGS. 10A and 10B show pre- and post-surgical corneal sensitivity data from area 9.
Figure 10B:
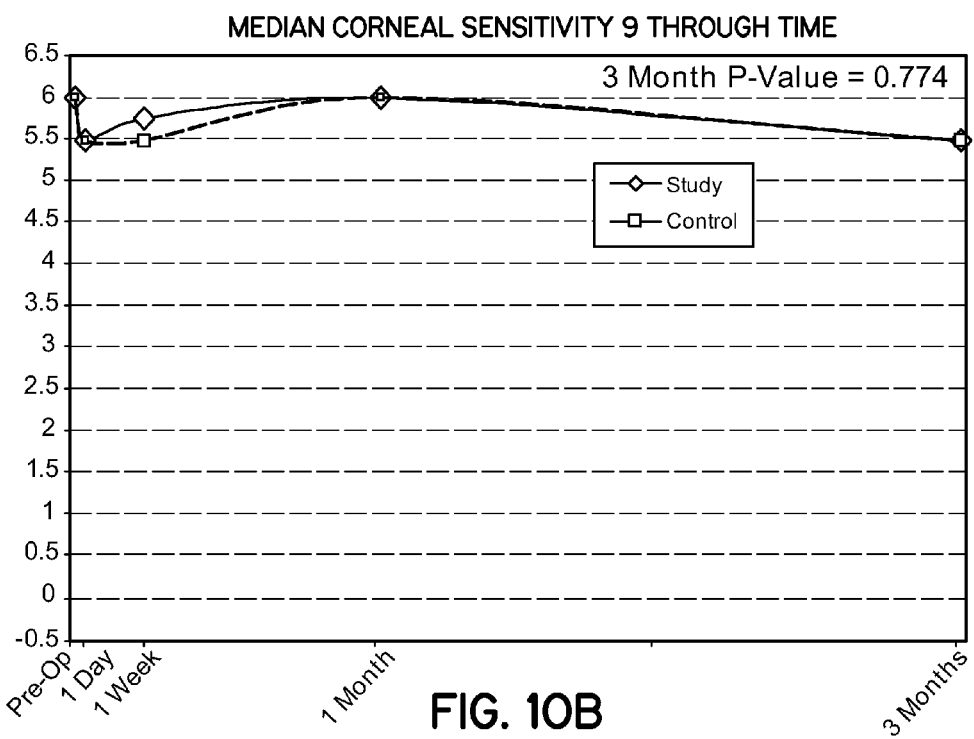

Data for each of the nine areas of the eye in which corneal sensitivity was assessed in each of the 19 control and 19 study eyes are shown in FIGS. 2-10. FIG. 2 shows pre- and post-LASIK surgery corneal sensitivity data from area 1 (one of the four quadrants of untreated cornea) for each study and control eye; at three months post-LASIK surgery, $p=0.272$. FIG. 3 shows pre- and post-LASIK surgery corneal sensitivity data from area 2 (a second of the four quadrants of untreated cornea) for each study and control eye; at three months post-LASIK surgery, $p=0.685$. FIG. 4 shows pre- and post-LASIK surgery corneal sensitivity data from area 3 (one of the four peripheral quadrants) for each study and control eye; at three months post-LASIK surgery, $p=0.049$. FIG. 5 shows pre- and post-LASIK surgery corneal sensitivity data from area 4 (a second of the four peripheral quadrants) for each study and control eye; at three months post-LASIK surgery, $p=0.020$. FIG. 6 shows pre- and post-LASIK surgery corneal sensitivity data from area 5 (center of the flap) for each study and control eye; at three months post-LASIK surgery, $p=0.009$. FIG. 7 shows pre- and post-LASIK surgery corneal sensitivity data from area 6 (a third of the four peripheral quadrants) for each study and control eye; at three months post-LASIK surgery, $p=0.013$. FIG. 8 shows pre- and post-LASIK surgery corneal sensitivity data from area 7 (the fourth of the four peripheral quadrants) for each study and control eye; at three months post-LASIK surgery, $p=0.013$. FIG. 9 shows pre- and post-LASIK surgery corneal sensitivity data from area 8 (a third of the four quadrants of untreated cornea) for each study and control eye; at three months post-LASIK surgery, $p=0.175$. FIG. 10 shows pre- and post-LASIK surgery corneal sensitivity data from area 9 (the fourth of the four quadrants of untreated cornea) for each study and control eye; at three months post-LASIK surgery, $p=0.774$.

Corneal sensitivity at each of the four peripheral quadrants of untreated cornea, shown in FIG. 1, over three months post-surgery was as follows: area 1 $p=0.272$, area 2 $p=0.685$, area 8 $p=0.175$, and area 9 $p=0.774$. These data indicated that all evaluated sites peripheral to (outside of) the flap area (areas 1, 2, 8, and 9) in the study eyes had no significant difference in corneal sensitivity ($p>0.05$) compared to the control eyes at all time points. Corneal sensitivity at each of the four peripheral quadrants, shown in FIG. 1, over three months post-surgery was as follows: area 3 $p=0.049$, area 4 $p=0.020$, area 6 $p=0.013$, and area 7 $p=0.013$. These data indicated that all evaluated sites within the flap area (areas 3, 4, 6, and 7) had statistically significant enhanced corneal sensitivity ($p<0.05$) in the study eyes versus control eyes. Corneal sensitivity at the center of the flap (area 5) over three months post-surgery was $p=0.009$. These data indicated that the point in the flap closest to the hinge had the least change in corneal sensitivity at all time points, and had the greatest difference between study and control eyes.

Patients were also evaluated by slit lamp examination. The eyelid margin, conjunctiva, cornea, and anterior segment were thoroughly examined. For each examination at all time points (pre-surgery and post-surgery one day, one week, one month, and three months) there were no statistically significant differences between the "study" and "control" eyes.

Patient subjective responses (pre-surgery and post-surgery one week, one month, and three months) to a questionnaire were evaluated. For each eye, patients were asked to rate (never, rarely, sometimes, often, all of the time) sensation (dry, sticky, gritty, sore, watery, burning, "foreign body"); vision (blurred); appearance (red, crusting or discharge on lashes); and sensitivity to light and wind/air conditioning. At all time points, there were no statistically significant differences between the "study" and "control" eyes with the exception of "foreign body sensation". This was more noticeable in the "study" eye one week post-surgery (p=0.047), although at one and three months post-surgery, there was no significant difference between the "study" and "control" eyes (p=0.102 and p=0.317, respectively).

These data demonstrated efficacy of topically applied cyclosporine 0.05% ophthalmic solution in significantly improved corneal sensitivity within three months post-LASIK. This provided strong evidence that cyclosporine 0.05% ophthalmic solution promoted corneal nerve recovery.

EXAMPLE 2

Photorefractive keratectomy (PRK) surgery is performed on at least one eye of a patient. In PRK, the corneal surface is reshaped using an Excimer laser for surface ablation and removal of the epithelium and stroma; it can also be performed under an epithelial flap. The protective superficial layers of the cornea heal post-operatively. Patients who have undergone PRK will typically require more time than patients who have undergone LASIK to achieve their best vision and restore corneal sensitivity. Outcomes of PRK and LASIK are comparable at the sixth postsurgical month. There may be a greater risk of scarring (haze) and unpredictable healing of the cornea with PRK. The risk of infection is also slightly higher with PRK than with LASIK, although infections following either procedure are rare.

After surgery, 0.05% cyclosporine is provided to the affected eye. Dosing intervals, assessment techniques, etc. are the same as in Example 1. Enhanced recovery rate of corneal sensitivity is provided.

EXAMPLE 3

Laser thermal keratoplasty (LTK) is performed on at least one eye of a patient. Energy from a holmium-YAG laser is applied in a predetermined pattern to shrink collagen fibers and thus steepen the cornea. After the procedure, 0.05% cyclosporine is provided to the affected eye. Dosing intervals, assessment techniques, etc. are the same as in Example 1. Enhanced recovery rate of corneal sensitivity is provided.

EXAMPLE 4

Conductive keratoplasty (CK) is performed on at least one eye of a patient. Low-level radiofrequency (RF) energy is administered through a fine probe. Using the probe, RF energy is applied to specific sites in a pre-set marked circular pattern (e.g., using a dye) on the outer cornea to shrink or ablate small areas of corneal tissue. The circular shrinkage pattern creates a constrictive band, thus increasing the overall curvature of the cornea.

After the procedure, 0.05% cyclosporine is provided to the affected eye. Dosing intervals, assessment techniques, etc. are the same as in Example 1. Enhanced recovery rate of corneal sensitivity is provided.

EXAMPLE 5

Laser-assisted in situ epithelial keratomileusis (LASEK) is performed on at least one eye of a patient. After surgery, 0.05% cyclosporine is provided to the affected eye. Dosing intervals, assessment techniques, etc. are the same as in Example 1. Enhanced recovery rate of corneal sensitivity is provided. Other variations or embodiments of the invention will also be apparent to one of ordinary skill in the art from the above description. As one example, the invention may be used to facilitate growth of transplanted neuronal cells, either mature or immature, and/or stem cells in the eye or brain. As another example, other ocular routes of administration and injection sites and forms are also contemplated. As another example, the invention may be used in patients who have experienced ocular trauma, ischemia, inflammation, etc. Thus, the forgoing embodiments are not to be construed as limiting the scope of this invention.

What is claimed is:

1. A method of enhancing the rate of restoration of corneal sensitivity in an eye of an individual after refractive surgery, the method comprising
topically administering cyclosporine to an eye of an individual having loss of corneal sensation after refractive surgery on the eye under conditions of at least daily dosing intervals in a therapeutic regimen for a duration sufficient to provide an enhanced rate of restoration of corneal sensitivity in the individual after refractive surgery, and assessing the enhanced rate of restoration of post-surgical corneal sensitivity.

2. The method of claim 1 wherein cyclosporine is administered at least substantially immediately after surgery and at least daily for up to at least one week after surgery.

3. The method of claim 1 wherein the restoration rate of post-surgical corneal sensitivity is enhanced compared to an eye not receiving cyclosporine.

4. The method of claim 1 wherein cyclosporine is administered starting at least on the day of surgery.

5. The method of claim 1, wherein the surgery is selected from laser-assisted in situ keratomileusis, laser-assisted in situ epithelial keratomileusis, and photorefractive keratectomy.

6. The method of claim 1, wherein the cyclosporin is administered as an emulsion having cyclosporine in a concentration ranging from 0.01% w/v to 1.0% w/v.

7. The method of claim 6, wherein the cyclosporin is administered at a concentration of 0.01% w/v.

8. The method of claim 6, wherein the cyclosporin is administered at a concentration of 0.05% w/v.

9. The method of claim 1, wherein the cyclosporin is administered as a solution having cyclosporine in a concentration ranging from 0.01% w/v to 1.0% w/v.

10. The method of claim 9, wherein the cyclosporin is administered at a concentration of 0.01% w/v.

11. The method of claim 9, wherein the cyclosporin is administered at a concentration of 0.05% w/v.

12. A method of enhancing the rate of restoration of corneal sensitivity, the method comprising
topically administering cyclosporine to an eye of an individual having loss of corneal sensation after refractive surgery on the eye,
and assessing the enhanced rate of restoration of post-surgical corneal sensitivity.

13. The method of claim 12, wherein the cyclosporin is administered as an emulsion having cyclosporine in a concentration ranging from 0.01% w/v to 1.0% w/v.

14. The method of claim 13, wherein the cyclosporin is administered at a concentration of 0.01% w/v.

15. The method of claim 14, wherein the cyclosporin is administered at a concentration of 0.05% w/v.

16. The method of claim 12, wherein the cyclosporin is administered as a solution having cyclosporine in a concentration ranging from 0.01% w/v to 1.0% w/v.

17. The method of claim 16, wherein the cyclosporin is administered at a concentration of 0.01% w/v.

18. The method of claim 17, wherein the surgery is selected from laser-assisted in situ keratomileusis, laser-assisted in situ epithelial keratomileusis, and photorefractive keratectomy.

19. The method of claim 16, wherein the cyclosporin is administered at a concentration of 0.05% w/v.

* * * * *